(12) United States Patent
Ueda

(10) Patent No.: US 10,716,929 B2
(45) Date of Patent: Jul. 21, 2020

(54) CONNECTOR AND MEDICAL DEVICE SET

(71) Applicant: TERUMO KABUSHIKI KAISHA, Tokyo (JP)

(72) Inventor: Yasuhiro Ueda, Kofu (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 15/701,067

(22) Filed: Sep. 11, 2017

(65) Prior Publication Data

US 2017/0368325 A1 Dec. 28, 2017

Related U.S. Application Data

(63) Continuation of application No. PCT/JP2016/001395, filed on Mar. 11, 2016.

(30) Foreign Application Priority Data

Mar. 11, 2015 (JP) .................................. 2015-048435

(51) Int. Cl.
*A61M 39/10* (2006.01)
*A61M 39/26* (2006.01)
(Continued)

(52) U.S. Cl.
CPC ............ *A61M 39/105* (2013.01); *A61M 5/14* (2013.01); *A61M 39/10* (2013.01);
(Continued)

(58) Field of Classification Search
CPC .............. A61M 5/1411; A61M 5/1413; A61M 5/16813; A61M 39/10; A61M 39/105;
(Continued)

(56) References Cited

U.S. PATENT DOCUMENTS 4,000,739 A * 1/1977 Stevens ................. A61M 25/00
600/433
4,013,310 A * 3/1977 Dye ....................... A61M 39/12
285/110
(Continued)

FOREIGN PATENT DOCUMENTS

CA 2932124 A1 * 6/2015 ............ A61M 39/24
CA 2982611 A1 * 10/2016 .......... A61M 39/223
(Continued)

OTHER PUBLICATIONS

International Search Report Issued in International Patent Application No. PCT/JP2016/001395 dated Jun. 7, 2016.

*Primary Examiner* — Nathan R Price
*Assistant Examiner* — Mark A Igel
(74) *Attorney, Agent, or Firm* — Foley & Lardner LLP

(57) ABSTRACT

A connector includes: a male connector portion; a first female connector portion; and a second female connector portion. The connector defines a flow path therein. The male connector portion is shaped to be connectable to a medical device female connector portion that is equal in shape to the first female connector portion. The male connector portion is shaped to not be connectable to a medical device female connector portion that is equal in shape to the second female connector portion.

15 Claims, 16 Drawing Sheets

(51) Int. Cl.
*A61M 39/22* (2006.01)
*A61M 5/14* (2006.01)
*A61M 5/168* (2006.01)

(52) U.S. Cl.
CPC ........ *A61M 39/1011* (2013.01); *A61M 39/22* (2013.01); *A61M 39/26* (2013.01); *A61M 5/1411* (2013.01); *A61M 5/1413* (2013.01); *A61M 5/16813* (2013.01); *A61M 2039/1038* (2013.01); *A61M 2039/1072* (2013.01); *A61M 2039/1077* (2013.01)

(58) Field of Classification Search
CPC .. A61M 39/1011; A61M 39/22; A61M 39/26; A61M 2039/1038; A61M 2039/1072; A61M 2039/1077; A61J 1/14–1493
USPC .................................................. 604/503–539
See application file for complete search history.

(56) References Cited

U.S. PATENT DOCUMENTS

| | | | |
|---|---|---|---|
| 4,114,853 A * | 9/1978 | Medvick | F16L 37/23 251/149.6 |
| 4,895,570 A * | 1/1990 | Larkin | A61M 39/1011 604/411 |
| D314,050 S * | 1/1991 | Sone | D24/129 |
| 5,137,524 A * | 8/1992 | Lynn | A61M 39/04 604/414 |
| 5,197,895 A * | 3/1993 | Stupecky | A61B 5/087 285/119 |
| 5,395,352 A * | 3/1995 | Penny | A61M 25/1025 137/606 |
| 5,437,650 A * | 8/1995 | Larkin | A61M 39/045 285/322 |
| 6,183,465 B1 * | 2/2001 | Meier | A61M 5/162 604/533 |
| 6,221,065 B1 * | 4/2001 | Davis | A61M 5/36 604/284 |
| 8,435,210 B2 * | 5/2013 | Zinger | A61J 1/2096 604/82 |
| 2002/0129858 A1 * | 9/2002 | Meyer | A61L 2/07 137/625.48 |
| 2006/0089603 A1 * | 4/2006 | Truitt | A61M 39/02 604/246 |
| 2008/0103484 A1 * | 5/2008 | Hishikawa | A61M 39/1011 604/533 |
| 2010/0318039 A1 * | 12/2010 | Hall | A61M 39/1011 604/246 |
| 2011/0233435 A1 * | 9/2011 | Matsumoto | A61M 39/045 251/192 |
| 2016/0305574 A1 * | 10/2016 | Burdge | A61M 39/18 |

FOREIGN PATENT DOCUMENTS

| | | | | |
|---|---|---|---|---|
| CA | 2982639 A1 * | 10/2016 | ......... | A61M 39/223 |
| DE | 102015205517 A1 * | 9/2016 | ............ | A61M 39/10 |
| JP | 2002-126094 | 5/2002 | | |
| JP | 2002126094 A * | 5/2002 | ......... | A61M 39/223 |
| JP | 2002-253669 | 9/2002 | | |
| JP | 2007-054093 | 3/2007 | | |
| JP | 2008-055056 | 3/2008 | | |
| JP | 2009-160452 | 7/2009 | | |
| JP | 2015073664 A * | 4/2015 | | |
| WO | WO-2008056631 A1 * | 5/2008 | ........ | A61M 39/1011 |
| WO | WO-2009093249 A1 * | 7/2009 | ............ | A61J 1/2096 |
| WO | WO-2012128321 A1 * | 9/2012 | ............ | F16L 23/003 |
| WO | WO-2013032714 A2 * | 3/2013 | ............ | A61M 39/223 |
| WO | WO-2013115293 A1 * | 8/2013 | ............ | A61M 39/26 |
| WO | WO-2013146753 A1 * | 10/2013 | ......... | F16K 11/0873 |
| WO | WO-2016116843 A1 * | 7/2016 | .............. | A61M 5/00 |
| WO | WO-2016152169 A1 * | 9/2016 | ................ | A61J 1/14 |
| WO | WO-2016157974 A1 * | 10/2016 | ............ | A61M 39/10 |

* cited by examiner

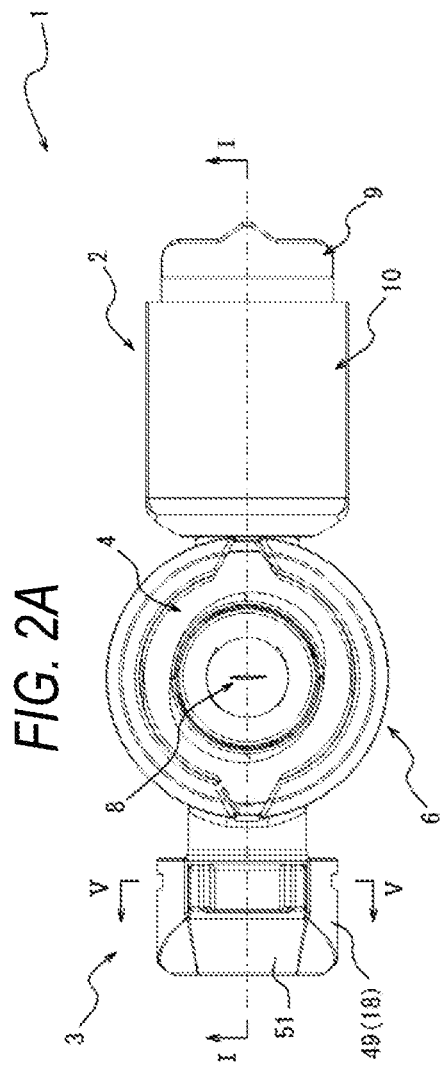
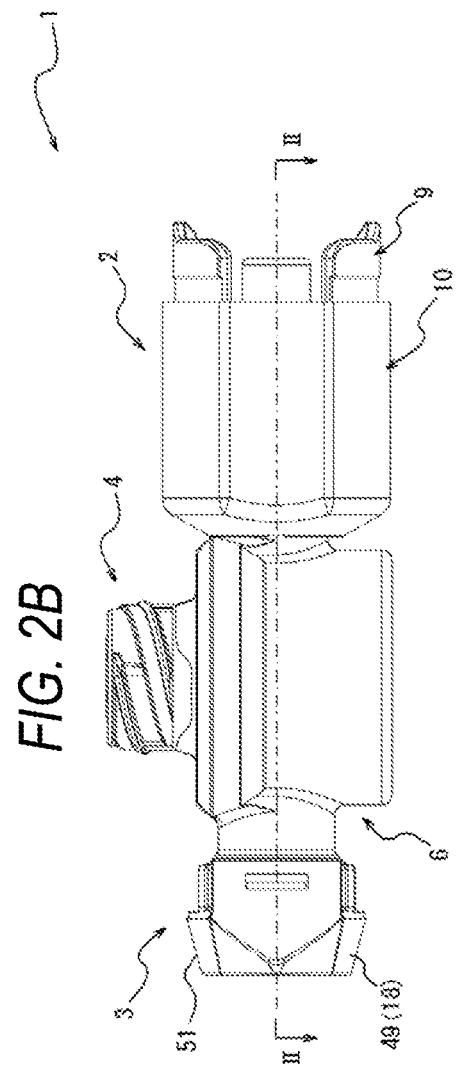
FIG. 2A
FIG. 2B

CONNECTOR AND MEDICAL DEVICE SET

CROSS-REFERENCE TO RELATED APPLICATIONS

The present application is a bypass continuation of PCT Application No. PCT/JP2016/001395, filed on Mar. 11, 2016, which claims priority to Japanese Application No. 2015-048435, filed on Mar. 11, 2015, the discloses of which are hereby incorporated by reference in their entireties.

BACKGROUND

The present application relates to a connector and a medical device set.

To provide an infusion such as a nutritional supplement or a medical fluid to a patient, there is the need to form a path for conveying the infusion (infusion line). The infusion line is generally formed by connecting infusion tubes and various medical devices. Conventionally, a connector is used to interconnect these different members.

In addition, the infusion line may be formed such that the upstream side of the infusion line is branched via a connector into a plurality of branch lines to administer a plurality of types of infusions to a patient, for example. JP 2009-160452 A describes forming an infusion line in such a manner that, when one branch line is added with a connector including a male connector portion, a first female connector portion almost coaxial to the male connector portion, and a second female connector portion almost axially orthogonal to the male connector portion, the connector is always provided with a port for an additional infusion tube.

SUMMARY

The branch lines need to connect to appropriate connection points in the connector depending on various circumstances such as a dose of an infusion per unit time according to a patient's condition and the type of the medical fluid, the possibility of addition of a branch line according to the patient's condition, and the ease of addition of a branch line.

However, when the connector disclosed in JP 2009-160452 A is used, the male connector portion of the connector can be connected to either the first female connector portion or the second female connector portion of another connector positioned more downstream of the infusion line than the former connector. This causes the problem that medical personnel may connect a branch line to an inappropriate point in the connector.

In view of the foregoing problem, the concepts described in this application have been devised to provide a connector and a medical device set that suppress medical personnel's mistake of connecting a branch line to an incorrect point in the connector at the time of formation of an infusion line.

In one embodiment, a connector includes a male connector portion, a first female connector portion, and a second female connector portion and defining a flow path therein, wherein the male connector portion is shaped to be connectable to a female connector portion in another medical device equal in shape to the first female connector portion and is not shaped to be connectable to a female connector portion in another medical device equal in shape to the second female connector portion.

In one aspect, the male connector portion includes a connection inhibition portion that, at the time of connection to a female connector portion in another medical device equal in shape to the second female connector portion, abuts with the female connector portion to inhibit the connection.

In one aspect, the male connector portion is provided at a first end side and the first female connector portion is provided at the second end side.

In one aspect, the connector includes a housing defining the flow path, wherein the housing constitutes a cylinder portion in the male connector portion at the first end side, defines a first insertion opening in the first female connector portion communicating with the flow path at the second end side, and defines a second insertion opening in the second female connector portion communicating with the flow path at a position different from the positions of the cylinder portion and the first insertion opening.

In one aspect, the connector includes a first elastic valve body that blocks the first insertion opening, and a second elastic valve body that blocks the second insertion opening.

In one aspect, the first female connector portion is shaped to be connectable to a male connector portion in another medical device connectable to the second female connector portion.

In one aspect, the first female connector portion includes a first engagement portion that engages with a male connector portion in another medical device equal in shape to the male connector portion at the time of connection and a second engagement portion that engages with a male connector portion in another medical device connectable to the second female connector portion at the time of connection.

In one aspect, the male connector portion includes an inhibition mechanism that, after connection to a female connector portion in another medical device equal in shape to the first female connector portion, inhibits the disconnection.

In another embodiments, a medical device set includes the connector, and a medical device with a female connector portion at a first end portion connected to the male connector portion of the connector.

In one aspect, the medical device set includes a second medical device that has at a first end portion a male connector portion connected to the first female connector portion of the connector when the medical device connected to the male connector portion of the connector is set as a first medical device.

In another embodiment, a medical device set includes the connector, a first medical device that has at a first end portion a female connector portion connectable to the male connector portion of the connector, and a second medical device that has at a first end portion a male connector portion that can be connected to and disconnected from the first female connector portion of the connector.

According to certain embodiments described in this application, it is possible to provide a connector and a medical device set that suppress medical personnel's mistake of connecting a branch line to an incorrect point in the connector at the time of formation of an infusion line.

BRIEF DESCRIPTION OF THE DRAWINGS

FIG. 2A is a diagram of the connector illustrated in FIG. 1 seen from the top of a second female connector portion, and FIG. 2B is a diagram of the connector illustrated in FIG. 1 seen from a side of the second female connector portion.

FIG. 14A illustrates a cover member in a second position, and FIG. 14B illustrates the cover member in a first position.

DESCRIPTION OF EMBODIMENTS

Figure 1A:
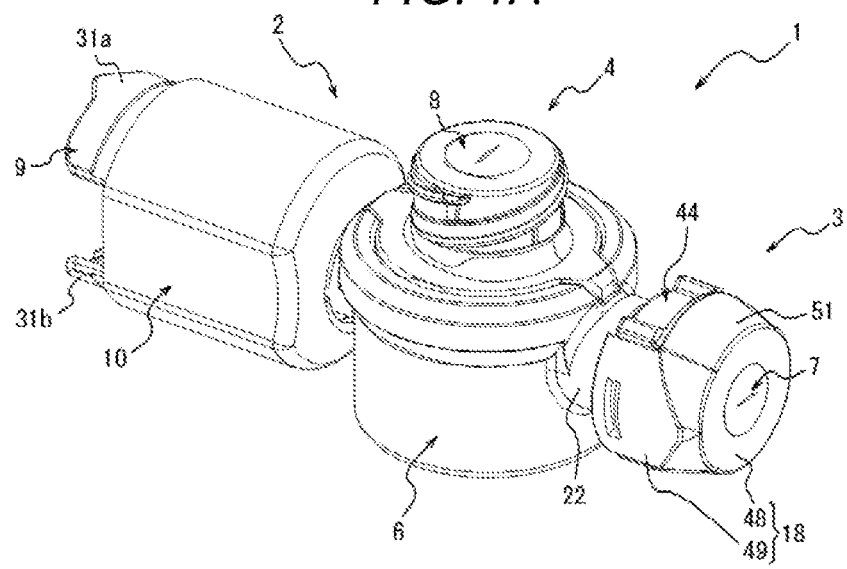
FIGS. 1A and 1B are perspective views of a connector according to one embodiment.

Embodiments of a connector and a medical device set will be described with reference to FIGS. 1 to 17. The same members in the drawings are given the same reference signs.

Figure 1B:
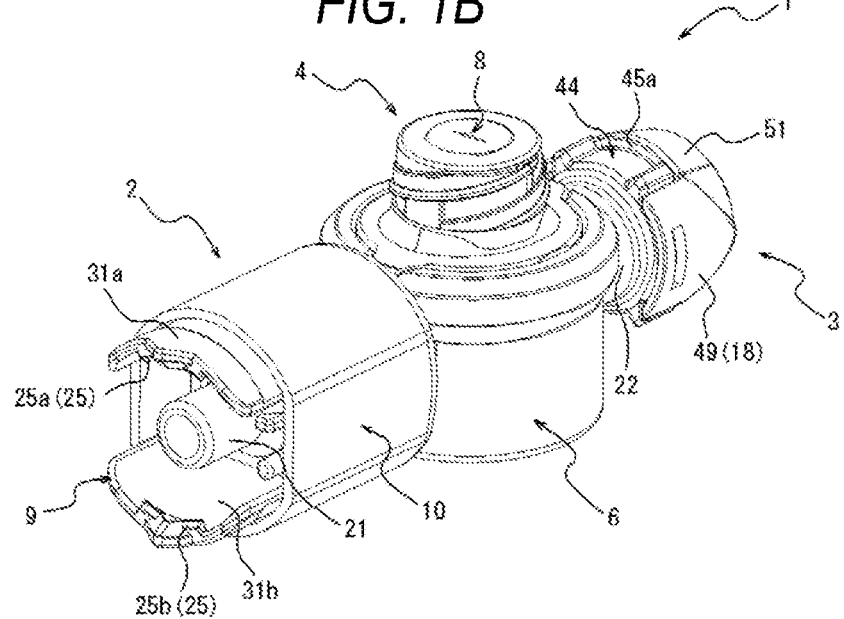

FIG. 1 is a perspective view of a connector 1 according to one embodiment, and FIGS. 1A and 1B illustrate the connector 1 seen from different viewpoints. As illustrated in FIG. 1, the connector 1 includes a male connector portion 2, a first female connector portion 3, and a second female connector portion 4. More specifically, the connector 1 of the embodiment includes the first female connector portion 3 as an upstream port portion, the male connector portion 2 as a downstream port portion, and the second female connector portion 4 as a coinfusion port portion.

Figure 3:
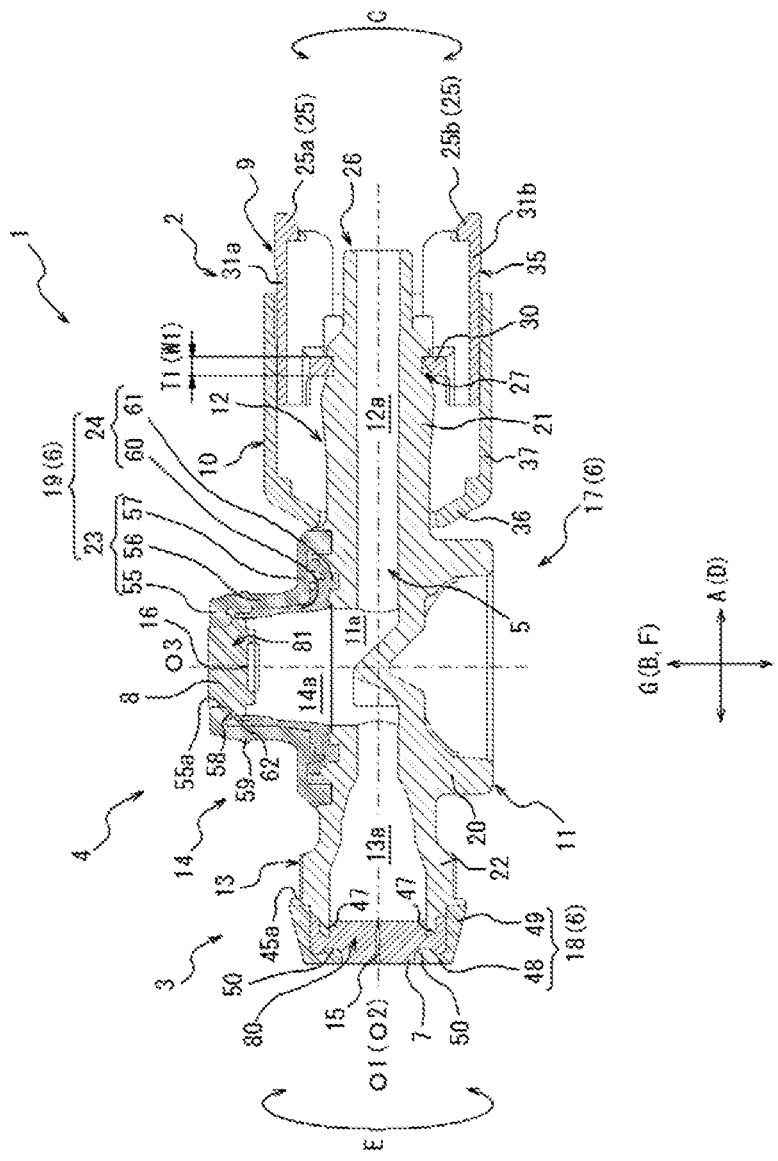
FIG. 3 is a cross-sectional view of FIG. 2A taken along line I-I.

FIG. 2A is a diagram of the connector 1 seen from the top of the second female connector portion 4, and FIG. 2B is a diagram of the connector 1 seen from a side of the second female connector portion 4. FIG. 3 is a cross-sectional view of FIG. 2A taken along line I-I, and FIG. 4 is a cross-sectional view of FIG. 2B taken along line II-II.

Figure 4:
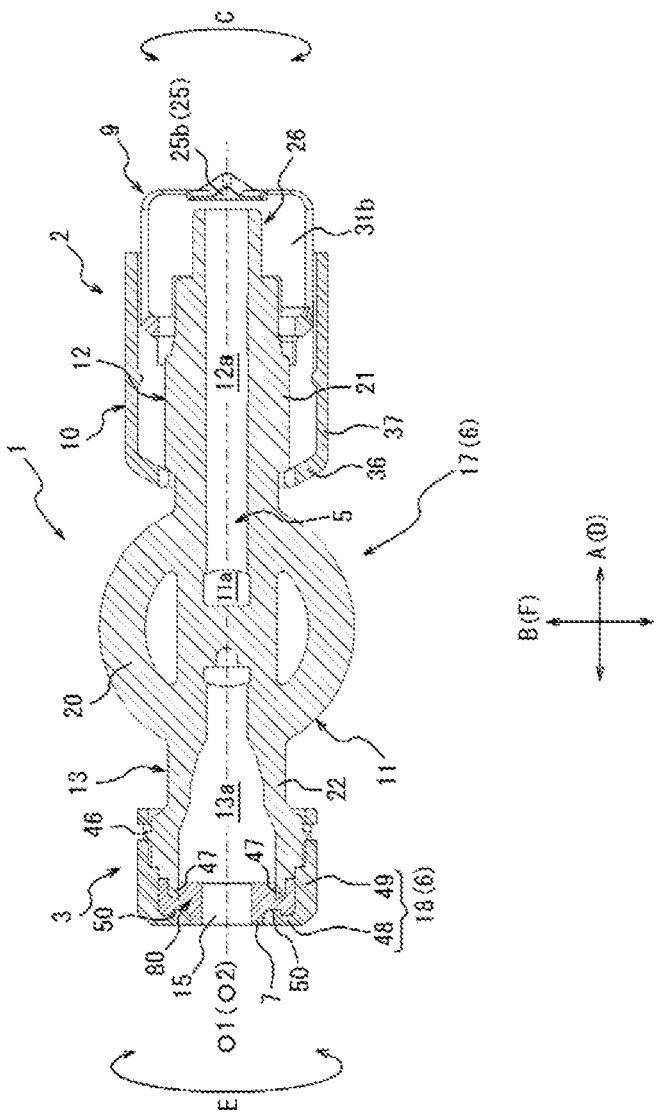
FIG. 4 is a cross-sectional view of FIG. 2B taken along line II-II.

As illustrated in FIGS. 1 to 4, the first female connector portion 3 and the second female connector portion 4 are different in shape. The male connector portion 2 is shaped to be connectable to a female connector portion in another medical device equal in shape to the first female connector portion 3, and is shaped not to be connectable to a female connector portion in another medical device equal in shape to the second female connector portion 4. Accordingly, to connect a plurality of connectors 1, for example, the male connector portion 2 of one connector 1 and the first female connector portion 3 of another connector 1 are connected together. The connection of the plurality of connectors 1 will be described later (see FIG. 11). As illustrated in FIGS. 3 and 4, the connector 1 defines a flow path 5 therein.

Herein, the "connectable shape" of the male connector portion to the female connector portion means the shape of the male connector portion that can be connected to the female connector portion in a liquid-tight manner such that an infusion such as a medical fluid does not leak at the portion of connection to the female connector portion. In addition, the "non-connectable shape" of the male connector portion to the female connector portion means the shape of the male connector portion that cannot be connected to the female connector portion in a liquid-tight manner such that an infusion does not leak at the portion of connection to the female connector portion.

Further, the "another medical device" is not limited to medical connectors such as a connector equal in shape to the connector 1 and a connector different in shape from the connector 1 but includes a medical tube and a syringe having a female connector portion equal in shape to the first female connector portion 3 and a female connector portion equal in shape to the second female connector portion 4, for example.

As illustrated in FIGS. 1 to 4, in the connector 1 of the embodiment, the male connector portion 2 is provided at a first end side of the connector 1, the first female connector portion 3 is provided at the second end of the connector 1, and the second female connector portion 4 is provided at a position in the connector 1 different from the positions of the male connector portion 2 and the first female connector portion 3.

Specifically, as illustrated in FIGS. 3 and 4, in the embodiment, a central axis line O1 of a first cylinder portion 12 described later in the male connector portion 2 is almost equal to a central axis line O2 of an inner wall defining a first insertion opening 80 described later in the first female connector portion 3. In the embodiment, the central axis line of the male connector portion 2 is almost equal to the central axis line O1 of the first cylinder portion 12 in the male connector portion 2, and the central axis line of the first female connector portion 3 is almost equal to the central axis line O2 of the inner wall defining the first insertion opening 80. Accordingly, the central axis line of the male connector portion 2 and the central axis line of the first female connector portion 3 are also almost equal to each other.

As illustrated in FIG. 3, in the embodiment, a central axis line O3 of an inner wall defining a second insertion opening 81 described later in the second female connector portion 4 is almost orthogonal to the central axis line O1 of the first cylinder portion 12 (or the central axis line O2 of the inner wall defining the first insertion opening 80). In the embodiment, the central axis line of the second female connector portion 4 is almost equal to the central axis line O3 of the inner wall defining the second insertion opening 81 in the second female connector portion 4, and the central axis line of the second female connector portion 4 and the central axis line of the male connector portion 2 are also almost orthogonal to each other. Further, the central axis line of the second female connector portion 4 and the central axis line of the first female connector portion 3 are almost orthogonal to each other. That is, the connector 1 of the embodiment is a T-shaped connector called T-shaped port.

The connector 1 of the embodiment is formed from a housing 6 defining the flow path 5 therein, a first elastic valve body 7 and a second elastic valve body 8 attached to the housing 6, a claw member 9 fixed to the housing 6, and a cover member 10 movably attached to the housing 6.

The housing 6 of the embodiment includes a housing trunk portion 11 that is almost circular cylindrical in outer shape, the first cylinder portion 12 that protrudes radially outward from the outer wall of the housing trunk portion 11, a second cylinder portion 13 that sandwiches the housing trunk portion 11 and protrudes radially outward from the outer wall of the housing trunk portion 11 at a position opposite to the first cylinder portion 12, and a third cylinder portion 14 that protrudes from the outer wall of the housing trunk portion 11 at a position different from the positions of the first cylinder portion 12 and the second cylinder portion 13.

The male connector portion 2 of the embodiment is formed from the first cylinder portion 12, the claw member 9, and the cover member 10 of the housing 6. The first female connector portion 3 of the embodiment is formed from the second cylinder portion 13 and the first elastic valve body 7 of the housing 6. The second female connector portion 4 of the embodiment is formed from the third cylinder portion 14 and the second elastic valve body 8 of the housing 6.

A trunk hollow portion 11a defined by the housing trunk portion 11, a first hollow portion 12a defined by the first cylinder portion 12, a second hollow portion 13a defined by the second cylinder portion 13, and a third hollow portion 14a defined by the third cylinder portion 14 communicate with each other. These hollow portions constitute the flow path 5 in the connector 1. The distal end side of the second hollow portion 13a in the second cylinder portion 13 constitutes the first insertion opening 80 into which the cylinder portion of a male connector portion having a predetermined shape such as that of the first cylinder portion 12 of the male connector portion 2, for example, is insertable from outside. The distal end side of the third hollow portion 14a in the third cylinder portion 14 constitutes the second insertion opening 81 into which the cylinder portion of a male connector portion having a predetermined shape different from that of the male connector portion 2 is insertable from outside.

The first elastic valve body 7 has a slit 15 that is elastically deformable to open or close when the cylinder portion of a male connector portion having a predetermined shape such as that of the first cylinder portion 12 of the male connector portion 2, for example, is inserted from outside, thereby blocking the first insertion opening 80. The second elastic valve body 8 has a slit 16 that is elastically deformable to open or close when the cylinder portion of a male connector portion having a predetermined shape different from the shape of the male connector portion 2 is inserted from the outside, thereby blocking the second insertion opening 81. The first insertion opening 80 is a space where the first elastic valve body 7 is positioned without insertion of the cylinder portion of a male connector portion, and the second insertion opening 81 is a space where the second elastic valve body 8 is positioned without insertion of the cylinder portion of a male connector portion. The flow path 5 in the connector 1 of the embodiment means the space in the housing 6 at the inner side of the first elastic valve body 7 and the second elastic valve body 8 without insertion of the cylinder portions of male connector portions into the first insertion opening 80 and the second insertion opening 81.

More specifically, the housing 6 of the embodiment includes a holder 17, and a first cap 18 and a second cap 19 supported by the holder 17. The holder 17 includes a holder main body 20 that is almost circular cylindrical in outer shape, a first holder cylinder portion 21 that is integrated with the holder main body 20 and is provided on the outer wall of the holder main body 20, and a second holder cylinder portion 22 that sandwiches the holder main body 20 and is provided on the outer wall of the holder main body 20 at a position opposite to the first holder cylinder portion 21. The first cap 18 is attached to the distal end of the second holder cylinder portion 22. The second cap 19 includes an upper cap 23 and a lower cap 24. The upper cap 23 and the lower cap 24 are attached to a first end side of the circular cylindrical holder main body 20.

Accordingly, in the embodiment, the first cylinder portion 12 of the housing 6 is formed from the first holder cylinder portion 21 of the holder 17, and the first hollow portion 12a defined by the first cylinder portion 12 of the housing 6 is the hollow portion defined by the first holder cylinder portion 21. In addition, the second cylinder portion 13 of the housing 6 in the embodiment is formed from the second holder cylinder portion 22 of the holder 17 and the first cap 18, and the second hollow portion 13a defined by the second cylinder portion 13 of the housing 6 is the hollow portion defined by the second holder cylinder portion 22 and the first cap 18. Further, in the embodiment, the third cylinder portion 14 of the housing 6 is formed from the upper cap 23 and the lower cap 24 of the second cap 19, and the third hollow portion 14a defined by the third cylinder portion 14 of the housing 6 is the hollow portion defined by the upper cap 23 and the lower cap 24 of the second cap 19. In the embodiment, the housing trunk portion 11 of the housing 6 is formed from the holder main body 20, and the trunk hollow portion 11a defined by the housing trunk portion 11 is defined by the holder main body 20.

Therefore, the male connector portion 2 of the connector 1 in the embodiment is formed from the first holder cylinder portion 21, the claw member 9, and the cover member 10 of the holder 17. In addition, the first female connector portion 3 of the connector 1 in the embodiment is formed from the second holder cylinder portion 22, the first cap 18, and the first elastic valve body 7 of the holder 17. Further, the second female connector portion 4 of the connector 1 in the embodiment is formed from the upper cap 23, the lower cap 24, and the second elastic valve body 8 of the second cap 19.

Examples of the material for the holder 17, the first cap 18, and the upper cap 23 and the lower cap 24 of the second cap 19 constituting the housing 6 may be, for example, various resin materials including: polyolefins such as polyethylene, polypropylene, and ethylene-propylene copolymer; ethylene-vinyl acetate copolymer (EVA); polyvinyl chloride; polyvinylidene chloride; polystyrene; polyamide; polyimide; polyamidimide; polycarbonate; poly-(4-methyl-pentene-1); ionomer; acrylic resin; polymethyl methacrylate; acrylonitrile-butadiene-styrene copolymer (ABS resin); acrylonitrile-styrene copolymer (AS resin); butadiene-styrene copolymer; polyesters such as polyethylene terephthalate (PET), polybutylene terephthalate (PBT), polycyclohexane terephthalate (PCT); polyether; polyether ketone (PEK); polyether ether ketone (PEEK); polyether imide; polyacetal (POM); polyphenylene oxide; modified polyphenylene oxide; polysulphone; polyether sulphone; polyphenylene sulfide; polyarylate; aromatic polyester (liquid crystal polymer); polytetrafluoroethylene, polyvinylidene fluoride, and other fluorine-based resins. In addition, a blend or a polymer alloy of one or more of the foregoing materials may be used. Alternatively, various glass materials, ceramics, or metallic materials may be used.

The first elastic valve body 7 and the second elastic valve body 8 are molded with molding dies in an elastically deformable manner. Examples of the material for the first elastic valve body 7 and the second elastic valve body 8 include, for example, various rubber materials such as natural rubber, isoprene rubber, butadiene rubber, styrene-butadiene rubber, nitrile rubber, chloroprene rubber, butyl rubber, acrylic rubber, ethylene-propylene rubber, hydrin rubber, urethane rubber, silicone rubber, fluorine rubber, and various thermal plastic elastomers such as styrene-based, polyolefin-based, polyvinyl chloride-based, polyurethane-based, polyester-based, polyamide-based, polybutadiene-based, trans polyisoprene-based, fluorine rubber-based, and chlorinated polyethylene-based elastomers. One of the foregoing materials maybe singly used or two or more of them maybe used in combination.

The hardness of the first elastic valve body 7 and the second elastic valve body 8 is preferably 20 to 60° (A hardness). Accordingly, the first elastic valve body 7 and the second elastic valve body 8 can have appropriate elasticity. This allows the first elastic valve body 7 and the second elastic valve body 8 to be elastically deformed at the insertion or removal of the cylinder portion of a male connector portion.

The claw member 9 and the cover member 10 can be formed from any of the same materials as those usable for the components of the housing 6 described above.

Hereinafter, the members of the connector 1 in the embodiment and the feature units formed from the members will be described in further detail.

Male Connector Portion 2

First, the configuration of the male connector portion 2 of the connector 1 in the embodiment will be described in detail. As illustrated in FIGS. 1 to 4, the male connector portion 2 in the embodiment includes the first holder cylinder portion 21 that protrudes outward from the outer wall of the holder main body 20 of the holder 17, the claw member 9 having a claw portion 25 that is attached to the outer wall of the first holder cylinder portion 21 and engages with a female connector portion equal in shape to the first female connector portion 3 at the time of connection to the female connector portion, and the cover member 10 that is positioned outside in a radial direction B of the first holder cylinder portion 21 and is attached to the holder 17 in such a manner as to be movable in a central axis line direction A of the first holder cylinder portion 21 between a first position located outside in the radial direction B of the claw portions 25 and a second position not located outside in the radial direction B of the claw portions 25.

First Holder Cylinder Portion 21

Figure 5:
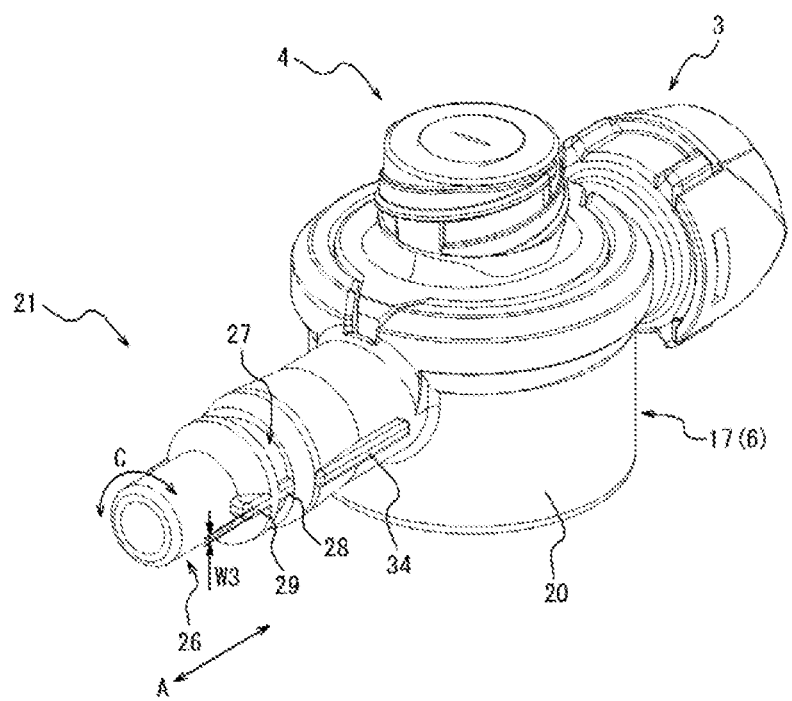
FIG. 5 is a perspective view of the connector illustrated in FIG. 1 from which a claw member and a cover member are removed.

FIG. 5 is a perspective view of the connector 1 from which the claw member 9 and the cover member 10 are removed. As illustrated in FIG. 5, the first holder cylinder portion 21 is almost circular cylindrical in shape and has a distal end portion 26 insertable into and removable from an insertion opening in a female connector portion equal in shape to the first female connector portion 3. In addition, as illustrated in FIGS. 3 and 5, the first holder cylinder portion 21 has long grooves 27 extending in the circumferential direction of the first holder cylinder portion 21 on the outer peripheral surface of a more proximal end side than the distal end portion 26 (the holder main body 20 side in the central axis line direction A). In the embodiment, the two long grooves 27 are provided at opposing positions on the transverse cross-sectional surface of the first holder cylinder portion 21 (the cross section orthogonal to the central axis line direction A). As illustrated in FIG. 5, the two long grooves 27 are separated from each other in the circumferential direction C of the first holder cylinder portion 21 by two division portions 28 intervening therebetween.

The male connector portion 2 also includes a connection inhibition portion that does not inhibit the connection to a female connector portion equal in shape to the first female connector portion 3 but inhibits the connection to a female connector portion equal in shape to the second female connector portion 4 by abutting with the female connector portion. In the embodiment, the male connector portion 2 includes the connection inhibition portion so that the male connector portion 2 cannot be connected to a female connector portion equal in shape to the second female connector portion 4. The connection inhibition portion may be designed to abut with a female connector portion equal in shape to the second female connector portion 4 at or during insertion of the male connector portion 2 into the female connector portion to restrict the movement of the male connector portion 2 in the direction of insertion into the female connector portion (in the embodiment, the same direction as one side of the central axis line direction A).

Specifically, the outer wall of the first holder cylinder portion 21 preferably has a protrusion portion as the connection inhibition portion that protrudes in the direction of crossing over the inner periphery of a first end portion of the second insertion opening 81 defined by a top plate portion 55 (see FIG. 3) of the upper cap 23 in the second female connector portion 4, or the inner wall of the member covering the first holder cylinder portion 21 (in the embodiment, the cover member 10 and the claw member 9) preferably has a protrusion portion as the connection inhibition portion that protrudes and abuts with the top plate portion 55 of the upper cap 23 in the second female connector portion 4. In the embodiment illustrated in FIGS. 4 and 5, the outer wall of the first holder cylinder portion 21 has a protrusion portion 29 as the connection inhibition portion protruding more outward in the radial direction B than the outer peripheral surface of the distal end portion 26, between the distal end portion 26 and the long grooves 27 and the division portions 28 in the central axis line direction A. The protrusion portion 29 does not inhibit the connection of the distal end portion 26 of the first holder cylinder portion 21 to a female connection portion equal in shape to the first female connector portion 3. However, when the distal end portion 26 of the first holder cylinder portion 21 is connecting to a female connector portion equal in shape to the second female connector portion 4, the protrusion portion 29 abuts with the upper surface (the upper surface in FIG. 3) of the top plate portion 55 of the upper cap 23 in the second female connector portion 4 to inhibit the further insertion of the distal end portion 26. The outer diameter of the distal end surface of the first holder cylinder portion 21 may be larger than the inner diameter of a first end portion of the second insertion opening 81 in the second female connector portion 4, and the inner diameter of a first end portion of the first insertion opening 80 may be sized such that the first holder cylinder portion 21 can be inserted therein. In such a case, the distal end surface of the first holder cylinder portion 21 abuts with the top plate portion 55 of the second female connector portion 4, and therefore the connection inhibition portion is formed from the distal end surface of the first holder cylinder portion 21.

In addition, as illustrated in FIG. 5, the outer wall of the first holder cylinder portion 21 has ribs 34 extending in the central axis line direction A at positions nearer the proximal end side than the long grooves 27 in the central axis line direction A. In the embodiment, the two ribs 34 are provided at opposing positions on the transverse section of the first holder cylinder portion 21.

Claw Member 9

Figure 6:
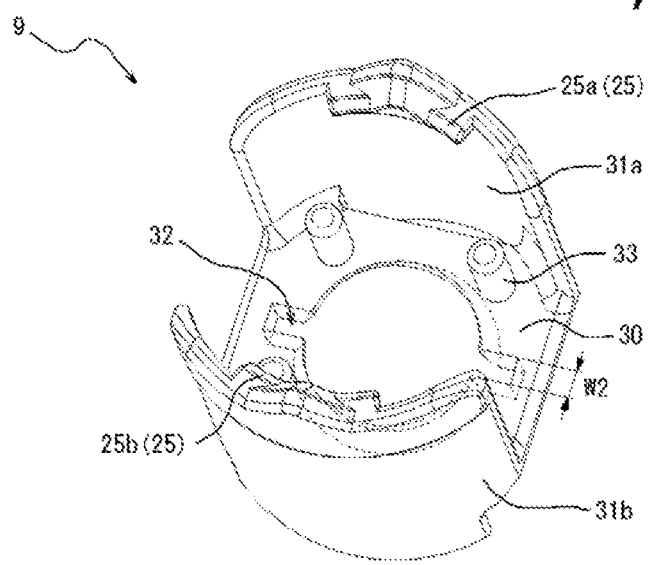
FIG. 6 is a perspective view of a single body of the claw member in the connector illustrated in FIG. 1.

FIG. 6 is a perspective view of a single body of the claw member 9. As illustrated in FIG. 6, the claw member 9 includes a flat bottom plate portion 30 that defines an almost circular opening in the center thereof and two curved plate-like side plate portions 31a and 31b that are erected and extended from opposing outer edges of the bottom plate portion 30 in a thickness direction of the bottom plate portion 30 (the same direction as the central axis line direction A in FIG. 3).

As illustrated in FIG. 3, the first holder cylinder portion 21 penetrates the opening in the bottom plate portion 30, and the inner edge portion of the bottom plate portion 30 defining the opening fits in the long grooves 27 formed on the outer peripheral surface of the first holder cylinder portion 21. This restricts the movement of the claw member 9 with respect to the holder 17 in the central axis line direction A of the first holder cylinder portion 21.

In addition, as illustrated in FIG. 6, the inner edge of the bottom plate portion 30 defining the opening, that is, the inner surface of the bottom plate portion 30 defining the central opening has concave portions 32 into which the division portions 28 of the first holder cylinder portion 21 (see FIG. 5) are fitted. Therefore, when the inner edge portion of the bottom plate portion 30 is fitted in the long grooves 27 on the outer peripheral surface of the first holder cylinder portion 21, the concave portions 32 formed in the inner edge of the bottom plate portion 30 fit with the division portions 28 of the first holder cylinder portion 21 to restrict the movement of the claw member 9 with respect to the holder 17 in the circumferential direction C of the first holder cylinder portion 21. In the embodiment, a thickness T1 of the bottom plate portion 30 (see FIG. 3) and a width W1 of the long grooves 27 (see FIG. 3) are almost equal, and a width W2 of the concave portion 32 in the bottom plate portion 30 oriented in the circumferential direction (see FIG. 6) and a width W3 of the division portions 28 oriented in the circumferential direction (see FIG. 5) are almost equal. Accordingly, the claw member 9 does not move with respect to the holder 17 in the central axis line direction A and the circumferential direction C of the first holder cylinder portion 21 but is fixed in position with respect to the holder 17.

In addition, as illustrated in FIG. 6, the upper surface of the bottom plate portion 30 (the surface positioned on the distal end portion 26 side of the first holder cylinder portion 21 in FIG. 3) has four projection portions 33 protruding in the central axis line direction. When the distal end portion 26 of the first holder cylinder portion 21 is connected to a female connector portion equal in shape to the first female connector portion 3, the distal end surfaces of the projection portions 33 abut with the upper surface of the first cap 18 in the first female connector portion 3 to inhibit further insertion of the distal end portion 26. This prevents the first elastic valve body 7 from being pushed unnecessarily into the distal end portion 26 and damaged.

As illustrated in FIGS. 3 and 6, the side plate portions 31a and 31b curve along the circumferential direction C of the first holder cylinder portion 21, and extend from the outer edge of the bottom plate portion 30 to the upper surface side and lower surface side of the bottom plate portion 30 (the holder main body 20 side in FIG. 3) in the central axis line direction A. The distal end portions of the side plate portions 31a and 31b (a first end portion of the first holder cylinder portion 21 on the distal end portion 26 side in FIG. 3) have claw portions 25 protruding toward the opposing side plates. Specifically, a claw portion 25a of one side plate portion 31a protrudes from the distal end portion of the side plate portion 31a toward the opposing other side plate portion 31b. A claw portion 25b of the other side plate portion 31b protrudes from the distal end portion of the side plate portion 31b to the opposing one side plate portion 31a. When the male connector portion 2 is connected to a female connector portion equal in shape to the first female connector portion 3, the claw portions 25a and 25b engage with level-difference portions 44 as engagement portions in the female connector portion. This will be described later in detail (see FIG. 1).

As illustrated in FIG. 3, the outer surfaces of the side plate portions 31a and 31b have level-difference surfaces 35 to restrict disconnecting of the cover member 10 described later.

Cover Member 10

Figure 7:
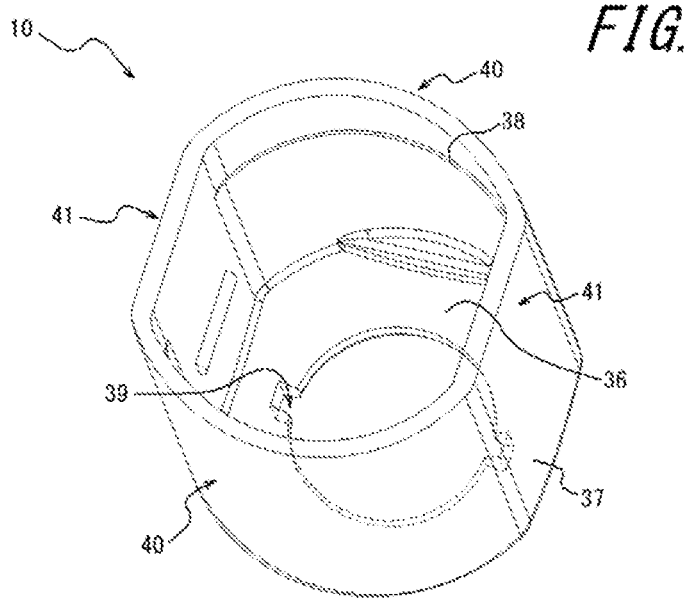
FIG. 7 is a perspective view of a single body of the cover member in the connector illustrated in FIG. 1.

FIG. 7 is a perspective view of a single body of the cover member 10. As illustrated in FIG. 7, the cover member 10 includes a bottom plate portion 36 that defines an almost circular opening in the center thereof and a cylindrical cover cylinder portion 37 that is integrated and connected with the outer edge of the bottom plate portion 36. As illustrated in FIGS. 3 and 4, the first holder cylinder portion 21 penetrates the opening in the bottom plate portion 36. The cover cylinder portion 37 is positioned outside in the radial direction B of the first holder cylinder portion 21 with respect to the first holder cylinder portion 21 and the side plate portions 31a and 31b, and surrounds the first holder cylinder portion 21 and the side plate portions 31a and 31b. In other words, the side plate portions 31a and 31b of the claw member 9 intervene between the inner wall of the cover cylinder portion 37 and the outer wall of the first holder cylinder portion 21. Further, the inner wall of the cover cylinder portion 37 is in abutment with the outer walls of the side plate portions 31a and 31b of the claw member 9.

In the cover member 10, the inner edge of the bottom plate portion 36, that is, the inner surface defining the opening can move in the central axis line direction A while sliding on the outer wall of the first holder cylinder portion 21. Specifically, the bottom plate portion 36 of the cover member 10 in the embodiment is movable between the outer wall of the holder main body 20 and the proximal ends of the side plate portions 31a and 31b of the claw member 9 (a first end on the holder main body 20 side in FIG. 3) in the central axis line direction A of the first holder cylinder portion 21. Along with the movement of the bottom plate portion 36 in the central axis line direction A, the cover cylinder portion 37 moves in the central axis line direction A while the inner surface of the cover cylinder portion 37 slides on the outer walls of the side plate portions 31a and 31b of the claw member 9.

The cover cylinder portion 37 of the cover member 10 is configured such that the inner wall of the cover cylinder portion 37 is movable in the central axis line direction A between a first position where the inner wall of the cover cylinder portion 37 is located outside in the radial direction B with respect to the claw portions 25 of the claw member 9 and a second position where the inner wall of the cover cylinder portion 37 is not located outside in the radial direction B with respect to the claw portions 25.

Specifically, in the embodiment, the upper surface of the bottom plate portion 36 (the surface on the distal end portion 26 side of the first holder cylinder portion 21 in FIG. 3) and the proximal ends of the side plate portions 31a and 31b of the claw member 9 are in abutment with each other in the first position. The inner wall of the cover cylinder portion 37 in the first position abuts with the outer walls of the side plate portions 31a and 31b in the radial direction B with respect to the claw portions 25.

Meanwhile, in the embodiment, the lower surface of the bottom plate portion 36 (the surface positioned on the holder main body 20 side in FIG. 3) and the outer peripheral surface of the holder main body 20 abut with each other in the second position (the position of the cover member 10 illustrated in FIG. 3). The inner wall of the cover cylinder portion 37 in the second position does not abut with the outer walls of the side plate portions 31a and 31b in a position outside in the radial direction B with respect to the claw portions 25.

That is, when the cover cylinder portion 37 is in the second position, the proximal end portions of the side plate portions 31a and 31b with the claw portions 25a and 25b are prone to elastically deform and expand outward in the radial direction B. Meanwhile, when the cover cylinder portion 37 is in the first position, as compared to the state in the second position, the proximal end portions of the side plate portions 31a and 31b are less prone to elastically deform and expand outward in the radial direction. In the male connector portion 2 of the embodiment, the position of the cover cylinder portion 37 can be switched between the first position and the second position, which improves operability for medical personnel in connecting and disconnecting the male connector portion 2 and a female connector portions equal in shape to the first female connector portion 3. This will be described later in detail (see FIG. 11).

Further, as illustrated in FIG. 7, the inner surface of the cover cylinder portion 37 has level-difference surfaces 38 that abut with the level-difference surfaces 35 of the claw member 9 (see FIG. 3) in the first position. In the cover member 10 of the embodiment, the upper surface of the bottom plate portion 36 abuts with the distal ends of the side plate portions 31a and 31b, and the level-difference surfaces 38 of the cover cylinder portion 37 abuts with the level-difference surfaces 35 formed on the outer walls of the side plate portions 31a and 31b, thereby suppressing disconnecting of the cover cylinder portion 37 from the first holder cylinder portion 21. In the embodiment, the disconnecting of the cover cylinder portion 37 from the first holder cylinder portion 21 is suppressed by both the abutment between the level-difference surfaces 35 of the claw member 9 and the level-difference surfaces 38 of the cover member 10 and the abutment between the distal ends of the side plate portions 31a and 31b of the claw member 9 and the upper surface of the bottom plate portion 36 of the cover member 10. However, the present invention is not limited to this configuration. Rather, the disconnecting of the cover cylinder portion 37 may be suppressed by either one of them.

As illustrated in FIGS. 3 and 4, the bottom plate portion 36 of the embodiment is tapered such that the inner edge portion of the bottom plate portion 36 is narrower than the outer edge portion of the bottom plate portion 36. In addition, as illustrated in FIG. 7, the inner edge of the bottom plate portion 36 defining the opening, that is, the inner surface of the bottom plate portion 36 defining the central opening has concave portions 39 into which the ribs 34 of the first holder cylinder portion 21 (see FIG. 5) fit. The cover member 10 is attached to the first holder cylinder portion 21 such that the concave portions 39 formed in the bottom plate portion 36 fit to the ribs 34 in the first holder cylinder portion 21, thereby to restrict the movement of the cover member 10 in the circumferential direction C with respect to the first holder cylinder portion 21.

Further, as illustrated in FIG. 7, the cover cylinder portion 37 of the cover member 10 is formed from opposing curve portions 40 and flat plate portions 41 that connect the opposing curve portions 40. In addition, the side plate portions 31a and 31b of the claw member 9 are arranged along the inner surfaces of the curve portions 40 of the cover cylinder portion 37 and abut with the same. Therefore, when an attempt to rotate the cover member 10 in the circumferential direction C is made, the both end portions of the side plate portions 31a and 31b of the claw member 9 oriented in the circumferential direction C and the inner surfaces of the flat plate portions 41 of the cover cylinder portion 37 abut and interfere with each other to restrict the rotation of the cover member 10 in the circumferential direction C.

In this way, the cover member 10 of the embodiment is configured not to rotate in the circumferential direction C with respect to the first holder cylinder portion 21 and the claw member 9 by both fitting the concave portions 39 in the bottom plate portion 36 to the ribs 34 in the first holder cylinder portion 21 and bringing the both ends of the side plate portions 31a and 31b in the claw member 9 oriented in the circumferential direction C into abutment and interference with the inner surfaces of the flat plate portions 41 of the cover cylinder portion 37. However, the present invention is not limited to this configuration. For example, the rotation of the cover member 10 in the circumferential direction C with respect to the first holder cylinder portion 21 and the claw member 9 may be restricted only by either one of the foregoing configurations.

First Female Connector Portion 3

Next, the first female connector portion 3 connectable to a male connector portion equal in shape to the male connector portion 2 will be further described in detail. The first female connector portion 3 of the embodiment includes the second holder cylinder portion 22 that protrudes outward from the outer wall of the holder main body 20 in the holder 17, the first cap 18 that is attached to the distal end of the second holder cylinder portion 22, and the first elastic valve body 7 that is positioned within the first insertion opening 80 defined by the second holder cylinder portion 22 and the first cap 18.

First Elastic Valve Body 7

Figure 8A:
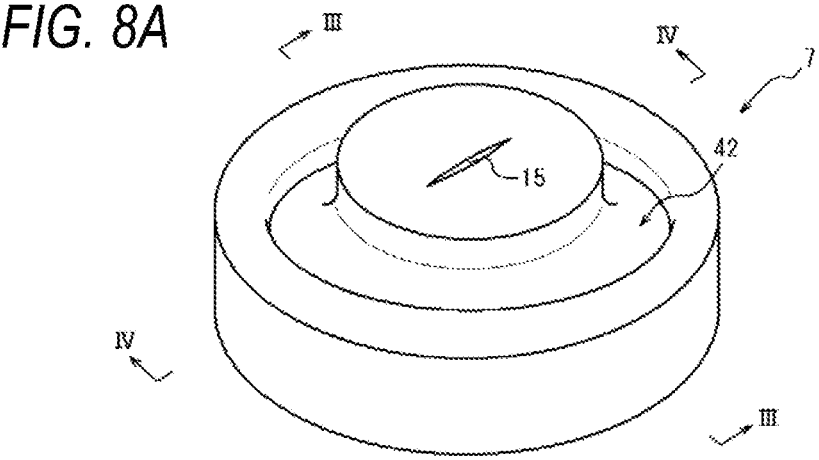
FIG. 8A is a perspective view of a single body of a first elastic valve body in the connector illustrated in FIG. 1.
Figure 8B:
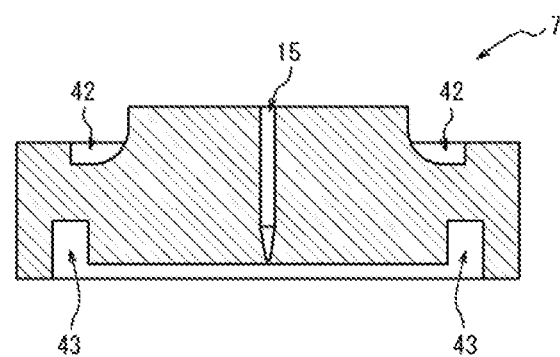
FIG. 8B is a cross-sectional view of FIG. 8A taken along line III-III.
Figure 8C:
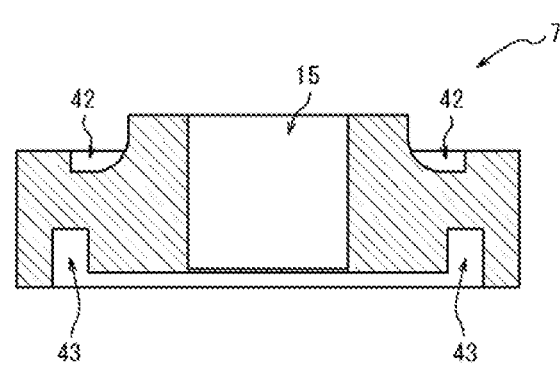
FIG. 8C is a cross-sectional view of FIG. 8A taken along line IV-IV.

FIG. 8A is a perspective view of a single body of the first elastic valve body 7, FIG. 8B is a cross-sectional view of FIG. 8A taken along line III-III, and FIG. 8C is a cross-sectional view of FIG. 8A taken along line IV-IV. As illustrated in FIG. 8, the first elastic valve body 7 is a circular flat elastic valve body. The first elastic valve body 7 has the straight-line slit 15 described above in the central region of the upper surface (the upper surface in FIG. 8 and the left surface in FIGS. 3 and 4) and has an upper annular groove 42 in the outer peripheral region on the periphery of the central region. The first elastic valve body 7 has also a lower annular groove 43 in the outer peripheral region of the lower surface opposite to the upper surface. The slit 15 is not formed in the central region of the lower surface. At the time of first insertion of a male connector portion, for example, the portion of the first elastic valve body 7 between the distal end of the slit 15 formed in the upper surface and the central region in the lower surface is tore down to let the slit 15 communicate from the upper surface to the lower surface. The step of letting the slit 15 penetrate the lower surface can be executed as part of the manufacturing process after completion of the molding of the first elastic valve body 7.

Second Holder Cylinder Portion 22

Figure 9:
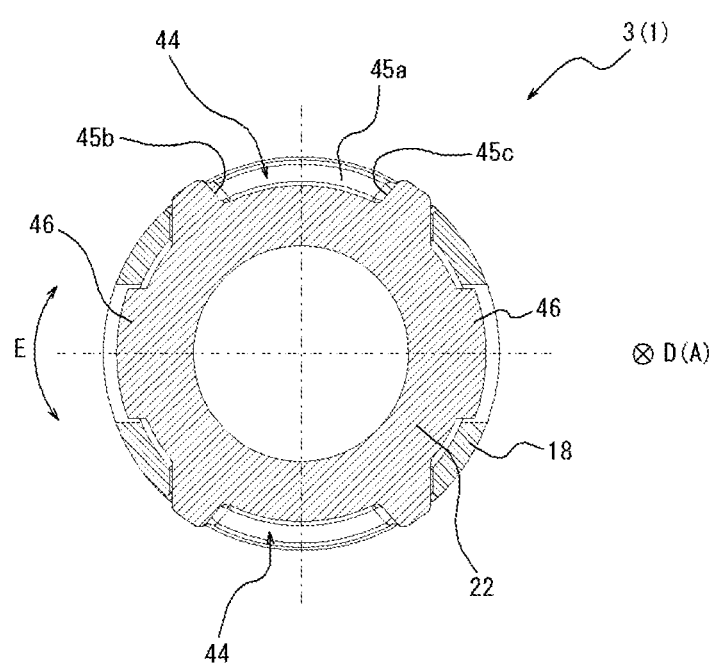
FIG. 9 is a cross-sectional view of FIG. 2A taken along line V-V.

FIG. 9 is a cross-sectional view of FIG. 2A taken along line V-V. As illustrated in FIGS. 1 and 9, the outer wall of the second holder cylinder portion 22 has the level-difference portions 44 in which the claw portions 25 of the claw member 9 get caught in and engage with a male connector portion equal in shape to the male connector portion 2 at the time of connection. In addition, as illustrated in FIG. 1B, the level-difference portions 44 of the embodiment are formed at positions corresponding to the two claw portions 25a and 25b of the male connector portion 2 (two upper and lower positions on the outer wall of the second holder cylinder portion 22 in FIG. 1B). As illustrated in FIG. 9, the level-difference portions 44 of the embodiment include first level-difference surfaces 45a on the distal end side of the second holder cylinder portion 22 oriented in a central axis line direction D of the second holder cylinder portion 22 (the same direction as the central axis line direction A of the first holder cylinder portion 21 and the central axis line direction of the inner wall defining the first insertion opening 80 in the embodiment), and second level-difference surfaces 45b and third level-difference surfaces 45c opposing to each other in a circumferential direction E of the second holder cylinder portion 22. The relationship in engagement between the claw portions 25 of the male connector portion 2 and the level-difference portions 44 will be described later in detail (see FIG. 11).

In addition, as illustrated in FIGS. 4 and 9, the outer wall of the second holder cylinder portion 22 has projection portions 46 that fit into the opening in the first cap 18 described later to fix the position of the first cap 18 with respect to the second holder cylinder portion 22. As illustrated in FIG. 9, the projection portions 46 of the embodiment are formed in positions almost equal to the positions of the level-difference portions 44 in the central axis line direction D of the second holder cylinder portion 22 and in positions different from the positions of the level-difference portion 44 in the circumferential direction E.

Further, as illustrated in FIGS. 3 and 4, the second holder cylinder portion 22 has at the distal end portion an annular lock projection 47 that compresses and sandwiches the first elastic valve body 7 in conjunction with the first cap 18. Specifically, the lock projection 47 enters into the lower annular groove 43 (see FIGS. 8B and 8C) in the first elastic valve body 7 to compress and sandwich the first elastic valve body 7 in conjunction with a lock projection 50 described later in the first cap 18.

First Cap 18

As illustrated in FIGS. 1, 3, and 4, the first cap 18 includes a top plate portion 48 defining an almost circular opening in the center and an almost circular cylindrical side wall portion 49 that is continued from the outer edge of the top plate portion 48.

The top plate portion 48 defines a first end portion of the first insertion opening 80 into which a male connector portion equal in shape to the male connector portion 2 is insertable, and has the annular lock projection 50 that protrudes toward the inside of the connector 1 oriented in the central axis line direction D at the lower end of the inner peripheral surface defining the first end portion of the first insertion opening 80 (the right end of the inner peripheral surface in FIGS. 3 and 4). The lock projection 50 enters into the upper annular groove 42 in the first elastic valve body 7 (see FIG. 8) and compresses and sandwiches the first elastic valve body 7 in conjunction with the lock projection 47 in the second holder cylinder portion 22 that enters into the lower annular groove 43 in the first elastic valve body 7 (see FIGS. 8B and 8C).

The side wall portion 49 is almost circular cylindrical in shape and defines the first insertion opening 80 in conjunction with the top plate portion 48. The second end of the side wall portion 49 opposite to the first end connected to the top plate portion 48 is attached to the second holder cylinder portion 22. Accordingly, the first cap 18 is supported by the second holder cylinder portion 22. The first cap 18 is preferably bonded to the second holder cylinder portion 22 by ultrasonic bonding or the like, for example. The first insertion opening 80 of the embodiment is defined by the second holder cylinder portion 22 and the first cap 18.

As illustrated in FIGS. 1 to 4, the outer wall of the side wall portion 49 of the first cap 18 has guide inclination surfaces 51 that are inclined with respect to the central axis line 02 and guides the claw portions 25a and 25b of the side plate portions 31a and 31b in the claw member 9 of the male connector portion 2 to the level-difference portions 44 of the second holder cylinder portion 22 at the time of connection to a male connector portion equal in shape to the male connector portion 2. Specifically, when a male connector portion equal in shape to the male connector portion 2 is connected to the first female connector portion 3, the first holder cylinder portion 21 of the male connector portion 2 is inserted into the first insertion opening 80 while elastically deforming the first elastic valve body 7, and the claw portions 25a and 25b of the side plate portions 31a and 31b of the male connector portion 2 slide on the guide inclination surfaces 51, and the distal end portions of the side plate portions 31a and 31b are guided to the level-difference portions 44 along the guide inclination surfaces 51 while the distal end portions are elastically deformed and expended outward in the radial direction B of the first holder cylinder portion 21 (outward in the radial direction F of the second holder cylinder portion 22 in the embodiment).

Then, when the claw portions 25a and 25b reach the level-difference portions 44 of the second holder cylinder portion 22, the claw portions 25a and 25b fit into the level-difference portions 44 and get caught in the first level-difference surfaces 45a of the level-difference portions 44 to complete connection of the male connector portion equal in shape to the male connector portion 2 and the first female connector portion 3.

The guide inclination surfaces 51 of the embodiment are formed at two opposing places on the outer wall of the side wall portion 49 corresponding to the positions of the claw portions 25a and 25b of the male connector portion 2 oriented in the circumferential direction of the first holder cylinder portion 21. However, the present invention is not limited to this configuration. The guide inclination surfaces 51 can be designed as appropriate according to the circumferential positons and number of the claw portions of the female connector portion shaped to be connectable to the first female connector portion 3.

Second Female Connector Portion 4

Next, the second female connector portion 4 will be described. The second female connector portion 4 of the embodiment includes the upper cap 23, the lower cap 24, and the second elastic valve body 8. The second female connector portion 4 of the embodiment is not connectable to a male connector portion equal in shape to the male connector portion 2 but is shaped to be connectable to a lock-type male connector portion prescribed in ISO594.

Second Elastic Valve Body 8

Figure 10A:
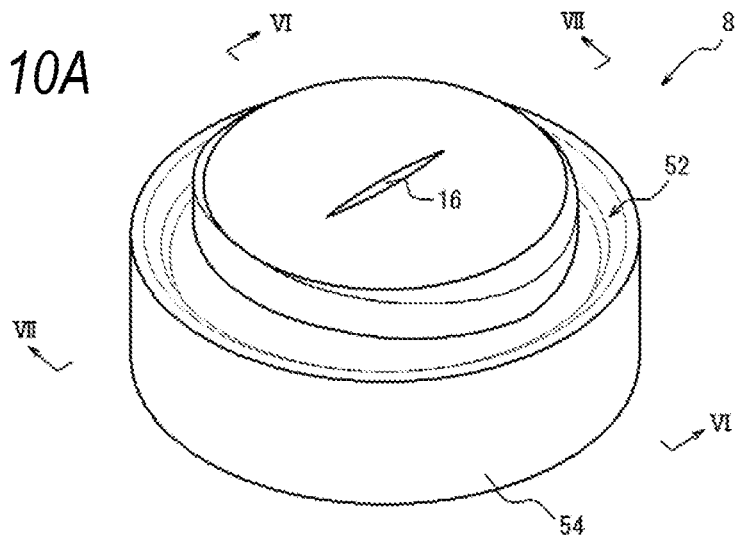
FIG. 10A is a perspective view of a single body of a second elastic valve body in the connector illustrated in FIG. 1, and FIGS. 10B and 10C are cross-sectional views of FIG. 10A taken along lines VI-VI and VII-VII.
Figure 10B:
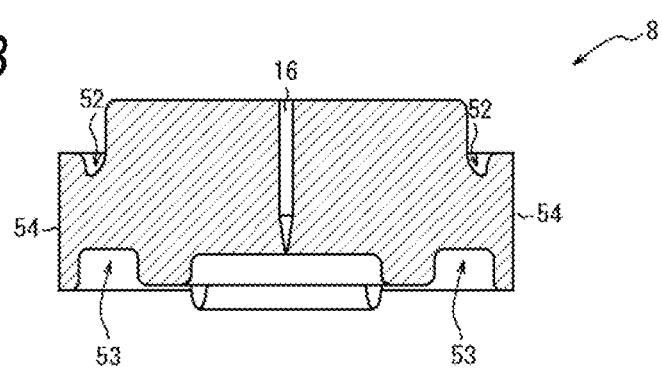
Figure 10C:
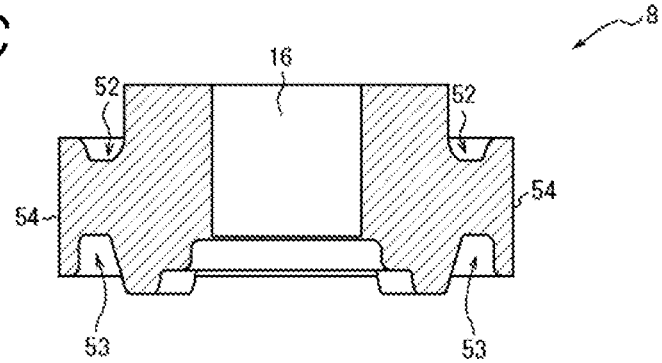

FIG. 10A is a perspective view of a single body of the second elastic valve body 8, and FIGS. 10B and 10C are cross-sectional views of FIG. 10A taken along lines VI-VI and VII-VII.

As illustrated in FIG. 10, the second elastic valve body 8 is a circular flat valve body and has an upper surface (the upper surface in FIG. 3) formed from a flat central region and an outer peripheral region positioned more outward in the radial direction than the central region.

The central region in the upper surface protrudes more outward (upward in FIG. 10) than the outer peripheral region and has a straight-line slit 16 in the central portion of the central region. The slit 16 is molded by a molding die and does not penetrate the lower surface at the time of molding but penetrates the lower surface at the first insertion of the male connector portion after the molding, for example. The step of letting the slit 16 penetrating the lower surface can be executed as part of the manufacturing process after completion of the molding.

As illustrated in FIG. 10, an upper annular groove 52 is formed in the outer peripheral region on the upper surface to surround the central region, and a lock projection 58 on the upper cap 23 (see FIG. 3) described later enters into the upper annular groove 52 to compress and sandwich the second elastic valve body 8 in conjunction with the lower cap 24.

The lower surface of the second elastic valve body 8 opposite to the upper surface has a flat central region and an outer peripheral region positioned more radially outward than the central region. The slit 16 is not formed in the central region of the lower surface. As described above, at the time of first insertion of a male connector portion, for example, the portion of the second elastic valve body 8 between the distal end of the slit 16 formed in the upper surface and the central region in the lower surface is tore down to let the slit 16 connect from the upper surface to the lower surface. A lower annular groove 53 is formed in the outer peripheral region on the lower surface to surround the central region, and a lock projection 62 on the lower cap 24 (see FIG. 3) described later enters into the lower annular groove 53 to compress and sandwich the second elastic valve body 8 in conjunction with the upper cap 23.

As illustrated in FIG. 10, the outer edge of the outer peripheral region on the upper surface of the second elastic valve body 8 and the outer edge of the outer peripheral region on the lower surface of the second elastic valve body 8 are connected to each other via an almost circular cylindrical peripheral surface 54 constituting the outer wall of the second elastic valve body 8 together with the upper surface and the lower surface.

Upper Cap 23

As illustrated in FIG. 3, the upper cap 23 includes a top plate portion 55, an almost circular cylindrical cylinder portion 56 that is connected to the outer edge of the top plate portion 55, and a flange portion 57 that is connected to the second end of the cylinder portion 56 opposite to the first end connected to the top plate portion 55. As illustrated in FIG. 3, the top plate portion 55 defines a first end portion of the second insertion opening 81 into which a male connector portion of a predetermined shape is insertable. The lower end of the inner peripheral surface of the top plate portion 55 (the lower side end of the inner peripheral surface in FIG. 3) defining the first end portion of the second insertion opening 81 has an annular lock projection 58 that protrudes toward the inside of the connector 1 oriented in a central axis line direction G of the inner wall defining the second insertion opening 81 (the direction orthogonal to the central axis line directions A and D and equal to the central axis line direction of the cylinder portion 56 in the embodiment). The lock projection 58 enters into the upper annular groove 52 in the second elastic valve body 8, and compresses and sandwiches the second elastic valve body 8 in conjunction with the lock projection 62 in the lower cap 24 that enters into the lower annular groove 53 in the second elastic valve body 8 (see FIG. 3).

In addition, as illustrated in FIG. 3, the inner peripheral surface 55a of the top plate portion 55 contacts the upper surface of the second elastic valve body 8 without connection to a female connector portion, and contacts an ISO594-prescribed female connector portion with connection to the female connector portion. Specifically, the central region on the upper surface of the second elastic valve body 8 fits into the space (the first end portion of the second insertion opening 81) surrounded by the inner peripheral surface 55a of the top plate portion 55 without connection to a male connector portion, and the outer peripheral surface of a male lure of an ISO-prescribed male connector portion contacts the inner peripheral surface 55a of the top plate portion 55 with connection to the ISO-prescribed male connector portion, and the male lure and the top plate portion 55 fit together. In the embodiment, the inner peripheral surface 55a of the top plate portion 55 is circular cylindrical in parallel to the central axis line direction G. Alternatively, the inner peripheral surface 55a of the top plate portion 55 may be tapered with gradual decrease in inner diameter with increasing proximity to the inside of the connector 1 in the central axis line direction G according to the outer shape of a male connector portion. In addition, in the embodiment, with connection to a male connector portion, the male connector portion fits to the upper cap 23 by the inner peripheral surface 55a of the circular cylindrical top plate portion 55. However, the present invention is not limited to this configuration, but with connection to a male connector portion, the male connector portion may not contact the inner peripheral surface of the top plate portion 55.

The outer peripheral surface of the cylinder portion 56 has a screw thread 59 to screw into an ISO594-prescribed lock connector. The flange portion 57 is a portion molded integrally with the cylinder portion 56. When the flange portion 57 engages with the holder main body 20, the upper cap 23 is held in the holder 17.

Lower Cap 24

As illustrated in FIG. 3, the lower cap 24 includes an almost circular cylindrical cylinder portion 60 and a flange portion 61 connected to a first end of the cylinder portion 60. The second end side of the cylinder portion 60 has an annular lock projection 62 that protrudes toward the outside of the connector 1 in the central axis line direction G (the upward direction in FIG. 3) and enters into the lower annular groove 53 in the second elastic valve body 8 to compress the second elastic valve body 8, and sandwich the second elastic valve body 8 in conjunction with the lock projection 58 of the upper cap 23. In this way, the second elastic valve body 8 is compressed and sandwiched in a sandwich portion formed from the lock projection 58 of the upper cap 23 and the lock projection 62 of the lower cap 24, and is fixed in position within the third hollow portion 14a, specifically, within the second insertion opening 81.

The lower cap 24 is held by the upper cap 23 by ultrasonic-bonding to the inner surface of the cylinder portion 56 of the upper cap 23 and/or the lower surface of the flange portion 57 (the lower surface in FIG. 3), and is fixed in position by holding the flange portion 61 of the lower cap 24 in the holder 17.

The holder 17 of the embodiment supports both the upper cap 23 and the lower cap 24 by direct contact with the two caps. Alternatively, for example, the holder 17 may contact directly only the lower cap 24 without contact with the upper cap 23 so that the upper cap 23 contacts the lower cap 24 and is supported by the lower cap 24. That is, the holder 17 may contact directly either one of the upper cap 23 and the lower cap 24 and support the one without direct contact with the other. The members to contact directly each other are bonded by ultrasonic bonding, for example.

In addition, in the embodiment, the upper cap 23 and the lower cap 24 sandwich the second elastic valve body 8 therebetween to hold the second elastic valve body 8 within the second insertion opening 81. Alternatively, for example, the second elastic valve body 8 may be compressed and sandwiched between a holder formed integrally by the holder 17 in the embodiment and the lower cap 24 and an upper cap as in the embodiment. That is, the housing 6 of the connector 1 in the embodiment is formed from the holder 17, the first cap 18, and the upper cap 23 and the lower cap 24 of the second cap 19. However, more than one of these members maybe integrally formed, and one of these members may be formed from a combination of two or more members.

Connection of the Connectors 1

As described above, the connector 1 of the embodiment includes the male connector portion 2, the first female connector portion 3, and the second female connector portion 4. The male connector portion 2 is shaped to be connectable to a female connector portion equal in shape to the first female connector portion 3 but is not shaped to be connectable to a female connector portion equal in shape to the second female connector portion 4. A configuration in which a plurality of connectors 1 of the embodiment is connected will be described below.

Figure 11:
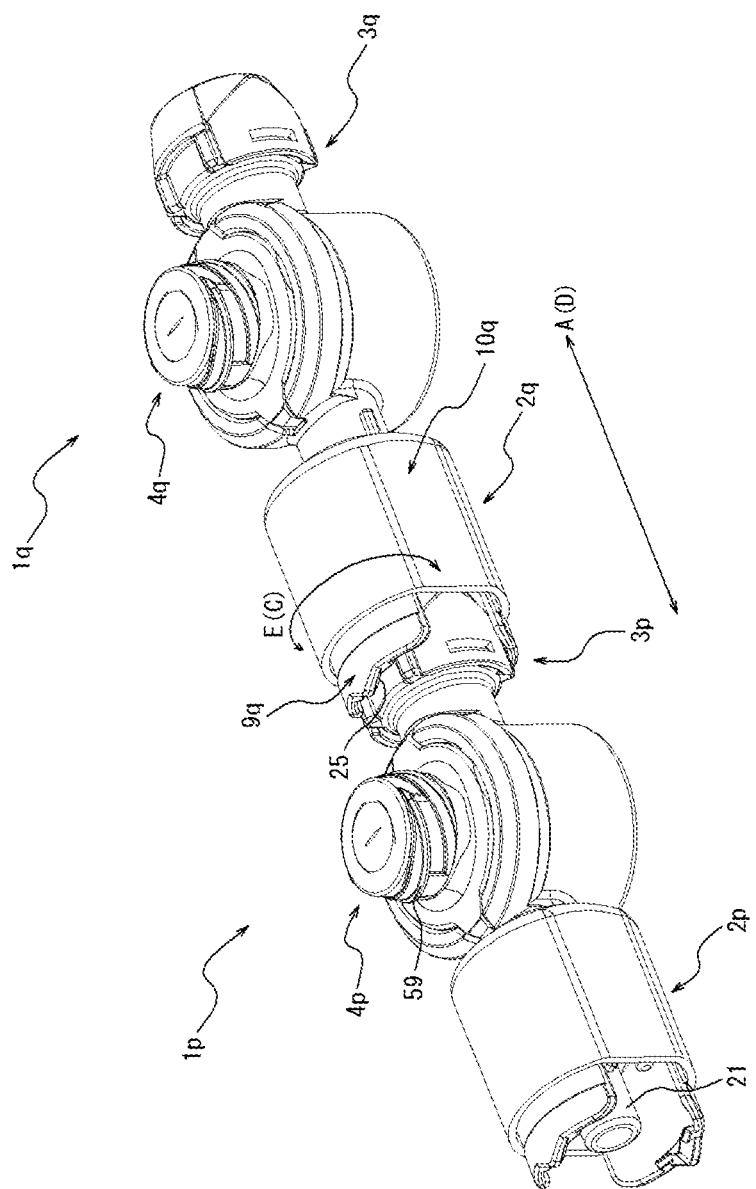
FIG. 11 is a perspective view of the connected connectors illustrated in FIG. 1.

FIG. 11 is a perspective view of connected connectors 1 of the embodiment. Connectors 1p and 1q are configured in the same manner as the connector 1, and detailed descriptions of the configuration of the connectors 1p and 1q will be omitted here.

As illustrated in FIG. 11, a first female connector portion 3p of the one connector 1p and a male connector portion 2q of the other connector 1q are connected together. FIG. 11 illustrates the state in which the first holder cylinder portion 21 (see FIG. 1B) of the male connector portion 2q of the other connector 1q is inserted into the first insertion opening 80 (see FIG. 3) in the first female connector portion 3p of the one connector 1p, and the claw portions 25 (see FIG. 1B) of the male connector portion 2q enter into the level-difference portions 44 (see FIG. 1) of the first female connector portion 3p. In other words, FIG. 11 illustrates the state in which the male connector portion 2q and the first female connector portion 3p are connected together.

In the state illustrated in FIG. 11, even when an attempt to move the male connector portion 2q distant from the first female connector portion 3p in the central axis line direction A (equal to the central axis line direction D) is made, the claw portions 25 of the male connector portion 2q abut with the first level-difference surfaces 45a of the level-difference portions 44 of the first female connector portion 3p (see FIG. 1B) to suppress the disconnecting of the male connector portion 2q from the first holder cylinder portion 21. Accordingly, even when the two connectors 1p and 1q are moved to be distant from each other in the central axis line direction A (equal to the central axis line direction D), no disconnection can be easily done.

In addition, in the state illustrated in FIG. 11, the male connector portion 2q of the other connector 1q has a cover member 10q in the second position. Moving the cover member 10q to the first position on the one connector 1p side in the central axis line direction A allows the inner wall of the cover member 10q to cover the outside of the claw portions 25 of a claw member 9q in the radial direction B (see FIG. 3). Accordingly, the elastic deformation and outward expansion in the radial direction B of the side plate portions 31a and 31b (see FIG. 3) of the claw member 9q are restricted. Therefore, the claw portions 25 are more unlikely to come off the level-difference portions 44, and the unnecessary disconnection of the male connector portion 2q and the first female connector portion 3p can be further suppressed.

With the cover member 10q in the first position, even when an attempt to rotate the male connector portion 2q of the other connector 1q in the circumferential direction E of the first female connector portion 3p (equal to the circumferential direction C) with respect to the first female connector portion 3p of the one connector 1p is made, the claw portions 25 of the male connector portion 2q abut with the second level-difference surfaces 45b or the third level-difference surfaces 45c (see FIG. 9) of the level-difference portions 44, and the cover member 10q restricts the elastic deformation of the distal end portions of the side plate portions 31a and 31b of the claw member 9q in such a manner as to expand outward in the radial direction B. Accordingly, the claw portions 25 do not come off the level-difference portions 44.

Meanwhile, with the cover member 10q in the second position, when an attempt to rotate the male connector portion 2q of the other connector 1q in the circumferential direction E with respect to the first female connector portion 3p of the one connector 1p is made, the claw portions 25 of the male connector portion 2q abut with the second level-difference surfaces 45b or the third level-difference surfaces 45c (see FIG. 9) of the level-difference portions 44. However, when rotational force is further added in the same direction, the claw portions 25 slide on the second level-difference surfaces 45b or the third level-difference surfaces 45c, and the distal end portions of the side plate portions 31a and 31b of the claw member 9q elastically deform and expand outward in the radial direction B to allow the claw portions 25 to be easily removed from the level-difference portions 44. That is, the first female connector portion 3p of the one connector 1p and the male connector portion 2q of the other connector 1q can be disconnected from each other by rotating the one connector 1p in the circumferential direction E relatively to the other connector 1q with the cover member 10q in the second position.

In contrast to this, when an attempt to connect the male connector portion 2q of the other connector 1q to a second female connector portion 4p of the one connector 1p is made, while the distal end portion 26 (see FIG. 3 and others) of the first holder cylinder portion 21 of the male connector portion 2q is inserted into the inside of the connector 1p from the second insertion opening 81 (see FIG. 3), the end portion of the protrusion portion 29 (see FIG. 5) of the first holder cylinder portion 21 of the male connector portion 2q on the distal end portion 26 side oriented in the central axis line direction A and the distal end surfaces of the projection portions 33 (see FIG. 6) of the claw member 9q abut with the upper surface of the top plate portion 55 (see FIG. 3) of the second female connector portion 4p before being positioned in the second female connector portion 4p of the first holder cylinder portion 21, and the distal end portion 26 of the first holder cylinder portion 21 cannot be further inserted into the inside of the connector 1p.

Therefore, the male connector portion 2q is made unable to connect to the second female connector portion 4p such that, for example, the first holder cylinder portion 21 is pushed outward from the second insertion opening 81 by resilience of the second elastic valve body 8 (see FIG. 3 and others) or the like, or the first holder cylinder portion 21 and the male connector portion 2q are kept integrated with each other in the state in which the first holder cylinder portion 21 is not fixed in position within the second female connector portion 4p and the first holder cylinder portion 21 is likely to come off the second female connector portion 4p to ensure insufficient liquid-tightness.

Therefore, even when medical personnel attempts by mistake to connect the male connector portion 2q of the other connector 1q to the second female connector portion 4p of the one connector 1p, the two cannot be connected to each other. Accordingly, it is possible to prevent medical personnel from mistaking the connection portion of a branch line to the other connector 1q.

The male connector portion 2q of the other connector 1q does not have a female screw portion that can screw into the screw thread 59 as a male screw portion of the second female connector portion 4p of the one connector 1p, and the second female connector portion 4p does not have engagement portions in which the claw portions 25 of the male connector portion 2q get caught. Accordingly, it is possible to suppress incorrect coupling of the two connectors 1p and 1q in which, even though the first holder cylinder portion 21 of the male connector portion 2q is likely to come off the second female connector portion 4p and the first holder cylinder portion 21 cannot ensure sufficient liquid-tightness, the position of the male connector portion 2q is fixed with respect to the second female connector portion 4p.

As described above, the connector 1 of the embodiment includes the first female connector portion 3 connectable to a male connector portion equal in shape to the male connector portion 2 and the second female connector portion 4 not connectable to a male connector portion equal in shape to the male connector portion 2. Accordingly, medical personnel can easily differentiate an infusion line including a plurality of medical tubes connected together using the male connector portion 2 and the first female connector portion 3 of the connector 1 from another infusion line including a medical tube connected using the second female connector portion 4 of the connector 1. This makes it possible to suppress wrong connection in the situation where these infusion lines need to be differentiated from each other to build the entire infusion line.

Further, the connector 1 of the embodiment has one male connector portion 2 and one first female connector portion 3. Therefore, for example, it is possible to form a main line for a high dose of infusion (an infusion line from an infusion holding instrument such as an infusion bag holding a infusion to an indwelling needle inserted in a patient) only using the male connector portion 2 and the first female connector portion 3 of the connector 1, and communicate a sub line for a relatively low dose of infusion or an infusion to be temporarily administered (an infusion line from an infusion holding instrument holding an infusion to the main line) to the main line via the second female connector portion 4. This allows medical personnel to form the infusion line with a clear distinction between the main line and the sub line.

Further, in the connector 1 of the embodiment, the male connector portion 2 and the first female connector portion 3 are linearly aligned such that the central axis line of the male connector portion 2 and the central axis line of the first female connector portion 3 are almost equal. Accordingly, two infusion tubes connected using the male connector portion 2 and the first female connector portion 3 of the connector 1 can also be almost linearly aligned to form the entire main line in a straight line. Accordingly, when the infusion holding instrument connected to the upstream end of the main line is hung down, for example, the main line extends perpendicularly in a straight line. In contrast, the central axis line of the second female connector portion 4 is inclined at a predetermined angle (about 90 degrees in the embodiment) with respect to the central axis lines of the male connector portion 2 and the first female connector portion 3. By positioning the male connector portion 2, the first female connector portion 3, and the second female connector portion 4 of the connector 1 in this relationship, the sub line connected from the second female connector portion 4 can be clearly differentiated as a branch line branched from the main line in terms of appearance.

The first female connector portion 3 of the embodiment is shaped to be connectable to a male connector portion equal in shape to the male connector portion 2 but is not shaped to be connectable to an ISO-standard lock-type male connector portion as a male connector portion connectable to the second female connector portion 4 of the embodiment. Specifically, the first female connector portion 3 of the embodiment does not have a male screw portion that can screw into a female screw portion of a lock-type male connector portion such as the screw thread 59 in the second female connector portion 4. Accordingly, a lock-type male connector portion cannot connect to the first female connector portion 3. That is, the male connector portion connectable to the first female connector portion 3 is different from the male connector portion connectable to the second female connector portion 4, which suppresses wrong connection in a further reliable manner.

Figure 12:
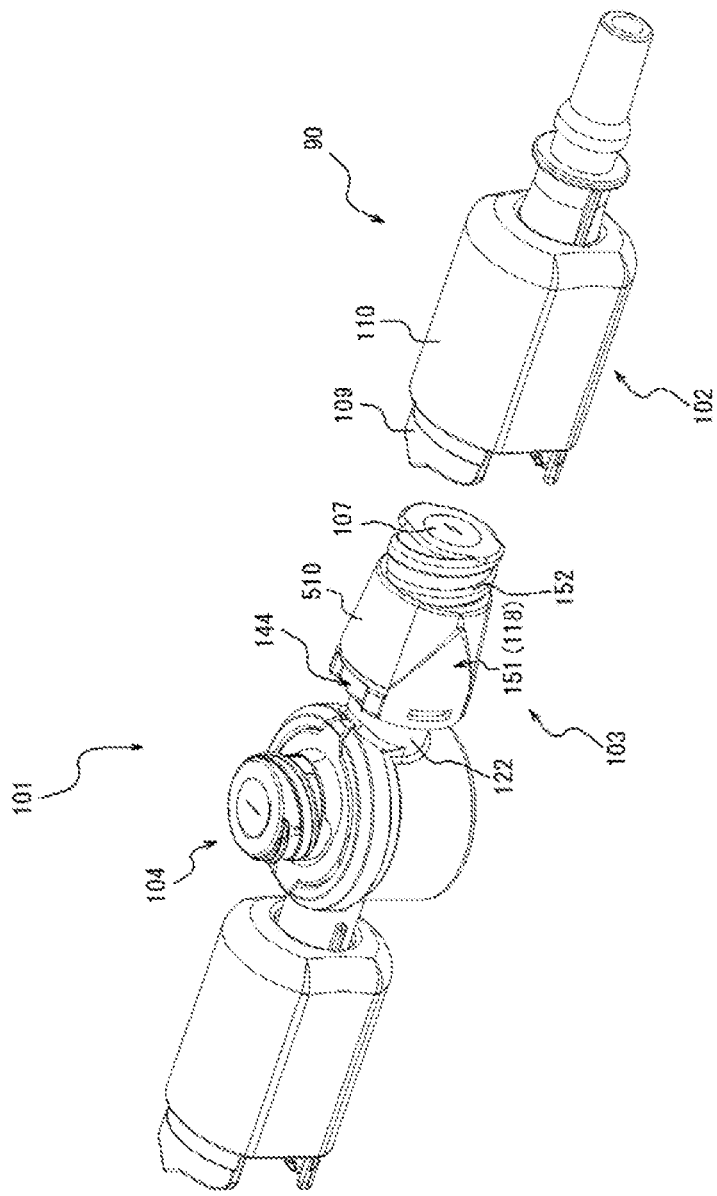
FIG. 12 is a perspective view of a connector as a modification example of the connector illustrated in FIG. 1.

However, the first female connector portion can be shaped to be connectable to a male connector portion connectable to the second female connector portion. FIG. 12 is a perspective view of a modification example of the first female connector portion 3 of the embodiment. A connector 101 illustrated in FIG. 12 includes a first female connector portion 103 different in shape from the first female connector portion 3 of the embodiment. The first female connector portion 103 illustrated in FIG. 12 is also shaped to be connectable to a male connector portion connectable to a second female connector portion 104. The first female connector portion 103 is partially different from the first female connector portion 3 of the embodiment in the shapes of the second holder cylinder portion, the first cap, and the first elastic valve body. The differences of the first female connector portion 103 from the first female connector portion 3 will be mainly described below and descriptions of the same parts will be omitted. FIG. 12 also illustrates a male connector 90 having at a first end side a male connector portion 102 equal in shape to the male connector portion 2 of the connector 1 in the embodiment.

Figure 13A:
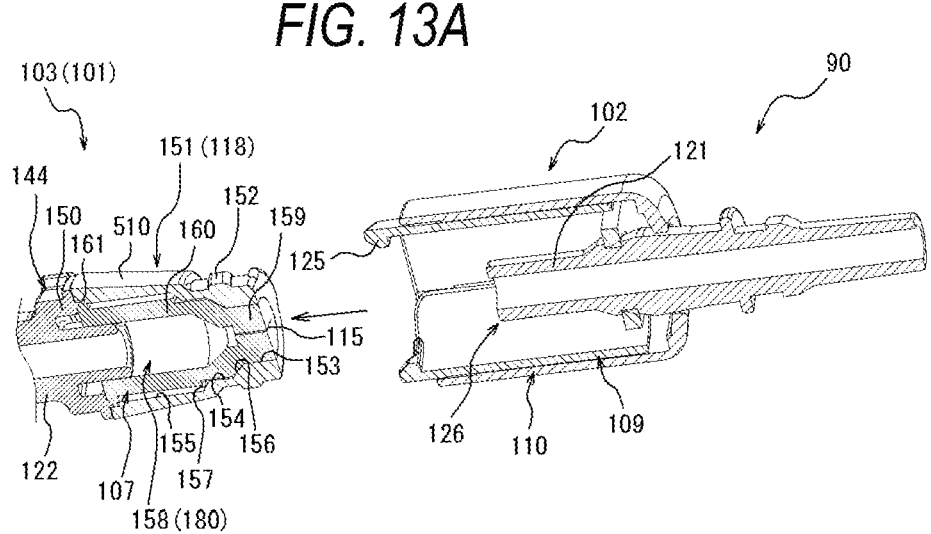
FIG. 13A is a cross-sectional perspective view of the connector and a male connector illustrated in FIG. 12 immediately before connection.
Figure 13B:
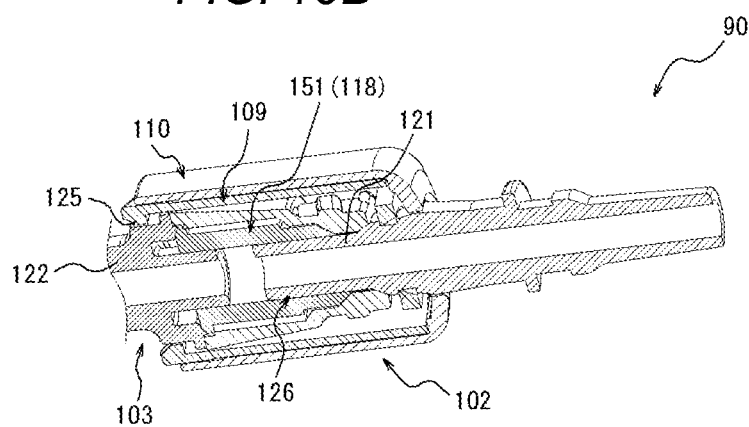
FIG. 13B is a cross-sectional perspective view of the connector and the male connector illustrated in FIG. 12 which are completely connected to each other.
Figure 14A:
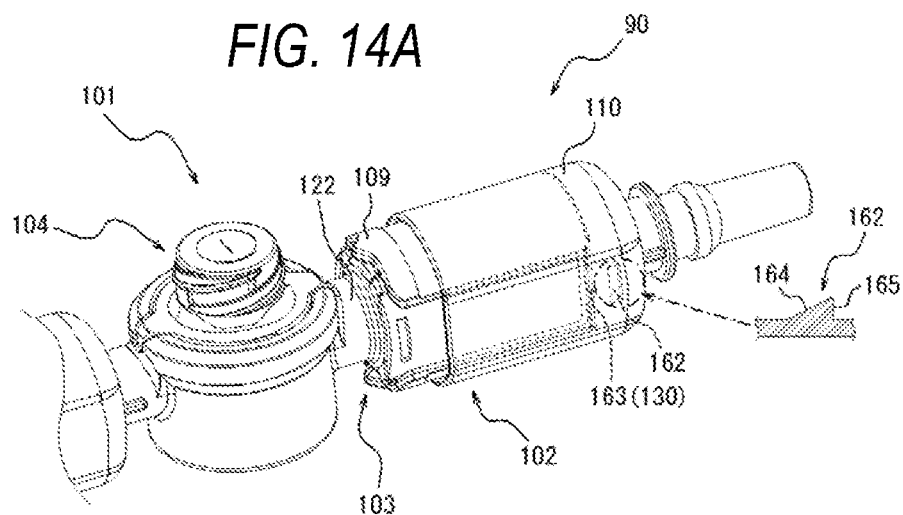
FIGS. 14A and 14B are perspective views of the connector and the male connector illustrated in FIG. 12 which are connected to each other.
Figure 14B:
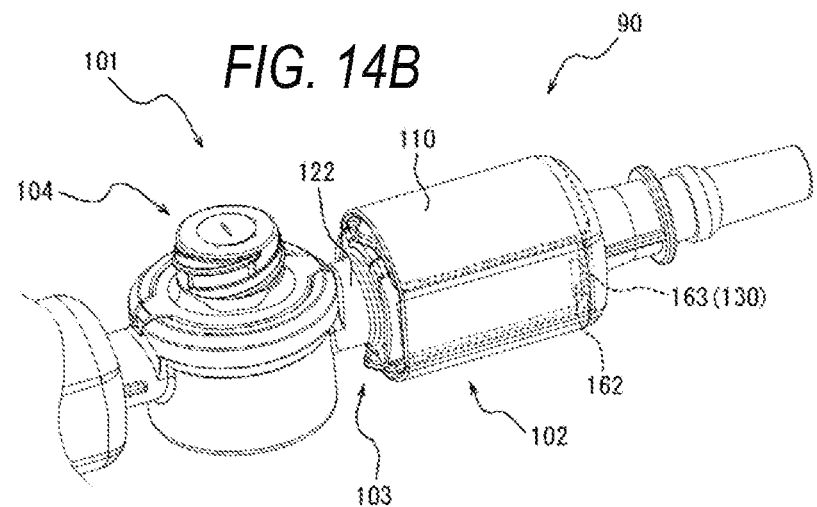

FIG. 13A is a cross-sectional perspective view of the connector 101 and the male connector 90 illustrated in FIG. 12 immediately before connection, and FIG. 13B is a cross-sectional perspective view of the connector 101 and the male connector 90 illustrated in FIG. 12 which are completely connected to each other as the male connector 90 is moved in an arrow direction illustrated in FIG. 13A. FIG. 14A illustrates the state in which the connector 101 and the male connector 90 illustrated in FIG. 12 are connected to each other and a cover member 110 in the male connector portion 102 of the male connector 90 is in the second position, and FIG. 14B illustrates the state in which the connector 101 and the male connector 90 illustrated in FIG. 12 are connected to each other and the cover member 110 in the male connector portion 102 of the male connector 90 is in the first position. FIG. 13B illustrates the state in which the cover member 110 is in the first position. For the sake of convenience, FIG. 14A includes an enlarged transverse sectional view of a projection portion 162 of the cover member 110.

The first female connector portion 103 illustrated in FIGS. 12 to 14 includes a second holder cylinder portion 122, a first cap 118, and a first elastic valve body 107 positioned in the first insertion opening 180.

As illustrated in FIG. 13, the outer wall of the second holder cylinder portion 122 has a flange portion 150 protruded radially outward, and the first cap 118 and the first elastic valve body 107 are supported on the flange portion 150. The first cap 118 is formed from an almost circular cylindrical cylinder body 151. A proximal end (a first end on the second holder cylinder portion 122 side) of the cylinder body 151 is attached to and supported on the flange portion 150 by ultrasonic bonding or the like, for example.

As illustrated in FIG. 12, the outer wall of the cylinder body 151 has guide inclination surfaces 510 that guide claw portions 125 of the male connector portion 102 (see FIG. 13) to level-difference portions 144. The cylinder body 151 has at a position nearer the distal end side than the guide inclination surfaces 510 (the end opposite to the proximal end) a screw thread 152 as a male screw portion capable of screwing into a female screw portion of an ISO-standard lock-type male connector portion.

As illustrated in FIG. 13A, the inner wall of the cylinder body 151 has a distal end portion 153 at the distal end side of the cylinder body 151, a middle portion 154 larger in inner diameter than the distal end portion 153, and a proximal end portion 155 further larger in inner diameter than the middle portion 154. A first diameter-increased portion 156 gradually increasing in inner diameter from the distal end portion 153 to the middle portion 154 is formed between the distal end portion 153 and the middle portion 154. A second diameter-increased portion 157 gradually increasing in inner diameter from the middle portion 154 to the proximal end portion 155 is formed between the middle portion 154 and the proximal end portion 155. The distal end portion 153, the first diameter-increased portion 156, the middle portion 154, the second diameter-increased portion 157, and the proximal end portion 155 define a communicating cylinder body hollow portion 158 that constitutes the first insertion opening 180 in the first female connector portion 103.

In addition, as illustrated in FIG. 13A, the first elastic valve body 107 includes an almost columnar head portion 159 with a slit 115 penetrating from the upper surface to the lower surface and a cylinder portion 160 having a first end connected to the outer edge of the lower surface of the head portion 159. The first elastic valve body 107 is accommodated in the cylinder body 151 as the first cap 118. Specifically, the head portion 159 of the first elastic valve body 107 is fitted and accommodated in a compressive-deformed state in the distal end portion 153 of the inner wall of the cylinder body 151. The cylinder portion 160 of the first elastic valve body 107 is accommodated in the first diameter-increased portion 156, the middle portion 154, the second diameter-increased portion 157, and the proximal end portion 155 of the inner wall of the cylinder body 151. The second end opposite to the first end of the cylinder portion 160 of the first elastic valve body 107 connected to the head portion 159 has a flange portion 161 extending radially outward from the outer wall of the cylinder portion 160. The flange portion 161 is compressed and sandwiched between the proximal end portion of the cylinder body 151 as the first cap 118 and the flange portion 150 of the second holder cylinder portion 122 to position the first elastic valve body 107 in the connector 101.

In addition, the distal end portion of the second holder cylinder portion 122 is fitted into the second end portion of the cylinder portion 160 of the first elastic valve body 107 such that the proximal end portion 155 of the inner wall of the cylinder portion 160 adheres closely to the outer wall of the distal end portion of the second holder cylinder portion 122. Accordingly, the cylinder body hollow portion 158 and the hollow portion in the second holder cylinder portion 122 communicate with each other in a liquid-tight manner.

The first female connector portion 103 of the connector 101 and the male connector portion 102 of the male connector 90 are connected in the same manner as the first female connector portion 3p of the connector 1p and the male connector portion 2q of the connector 1q are connected (see FIG. 13). That is, when a distal end portion 126 of a first holder cylinder portion 121 of the male connector portion 102 is inserted into the cylinder body hollow portion 158 and the claw portions 125 fit into the level-difference portions 144, the first female connector portion 103 and the male connector portion 102 are connected.

The operation of the cover member 110 is the same as the operation of the cover member 10q of the connector 1q. Moving the position of the cover member 110 from the second position (see FIG. 14A) to the first position (see FIG. 14B), the first female connector portion 103 of the connector 101 and the male connector portion 102 of the male connector 90 can be firmly connected.

However, the male connector portion 102 illustrated in FIGS. 12 to 14 has the projection portion 162 (see FIG. 14) that protrudes toward the inner wall of the cover member 110. When the cover member 110 is moved from the second position to the first position, the projection portion 162 slides and gets over an outer edge portion 163 (see FIG. 14) of a bottom plate portion 130 of a claw member 109. Accordingly, even though an attempt to move the cover member 110 again from the first position to the second position is made, the projection portion 162 abuts with the upper surface of the bottom plate portion 130 to inhibit the movement of the cover member 110 to the second position. In other words, the male connector portion 102 includes an inhibition mechanism that, after the connection to the first female connector portion 103 of the connector 101, inhibits the disconnection from the first female connector portion 103. In the example illustrated in FIG. 14, the inhibition mechanism is formed from the outer edge portion 163 of the bottom plate portion 130 of the claw member 109 and the projection portion 162 of the cover member 110. Accordingly, once the cover member 110 is moved from the second position to the first position, the cover member 110 cannot be moved again from the first position to the second position. Therefore, the first female connector portion 103 and the male connector portion 102 illustrated in FIGS. 12 to 14 are connected and the cover member 110 is moved to the first position so that the two cannot be disconnected by a normal operation. Alternatively, the inhibition mechanism such as the projection portion 162 and the outer edge portion 163 can be provided in the first female connector portion 3 and the male connector portion 2 of the embodiment.

In addition, the inhibition mechanism is not limited to the foregoing configuration as far as the inhibition mechanism does not have a mechanism allowing disconnection of two connected portions so that the two portions cannot be separated by an external force of a predetermined value or lower (for example, 30 Nor less). The surface of the projection portion 162 sliding on the bottom plate portion 130 to move the cover member 110 from the second position to the first position is set as a surface 164 inclined with respect to the direction of the movement, and the surface of the projection portion 162 abutting with the upper surface of the bottom plate portion 130 to move the cover member 110 from the first position to the second position is set as a surface 165 almost perpendicular to the direction of the movement and almost parallel to the upper surface of the bottom plate portion 130, whereby the two portions cannot be separated by an external force of a predetermined value or less (see the enlarged cross-sectional view of the projection portion 162 in FIG. 14A).

To connect an ISO594-prescribed lock-type male connector portion connectable to the second female connector portion 104 to the first female connector portion 103 of the connector 101, the male lure of the male connector portion is inserted into the cylinder body hollow portion 158 while elastically deforming the first elastic valve body 107, and the flow path in the male lure of the male connector portion communicates with the flow path in the connector 101 through the slit 115 in a liquid-tight manner. FIG. 13 does not illustrate the shape and deformation of the first elastic valve body 107 in detail. For example, the cylinder portion 160 is formed in a bellows shape to elastically deform when the head portion 159 is pushed into the cylinder body hollow portion 158 so that the head portion 159 can be moved toward the inside of the cylinder body hollow portion 158 while the cylinder portion 160 is compressed and deformed to open the slit 115. More specifically, by moving the head portion 159 from the region defined by the distal end portion 153 to the region defined by the middle portion 154, the head portion 159 compressive-deformed and pushed in the region defined by the distal end portion 153 expands radially outward to open the slit 115.

In the state in which the first female connector portion 103 and the male lure of the ISO-standard male connector portion are coupled in a liquid-tight manner, the female screw portion of the male connector portion is screwed into the screw thread 152 as the male screw portion formed on the outer wall of the cylinder body 151 of the first female connector portion 103. Accordingly, the first female connector portion 103 of the connector 101 and the ISO-standard male connector portion can be fixed while the flow path in the male lure of the male connector portion remains in communication with the flow path in the connector 101 in a liquid-tight manner.

Specifically, the first female connector portion 103 includes the level-difference portions 144 as first engagement portions to engage with the male connector portion 102 at the time of connection and the male screw portion (screw thread 152) as a second engagement portion to engage with the ISO-standard lock-type male connector portion as a male connector portion connectable to the second female connector portion 104 at the time of connection. The first female connector portion 103 is shaped to be connectable not only to the male connector portion 102 but also to the male connector portion connectable to the second female connector portion 104.

The connectors 1, 1p, 1q, and 101 of the embodiment are all T-shaped connectors. However, the connector of the present invention is not limited to T-shaped connectors but may be formed from a three-way stopcock including a cock and a holder accommodating the cock and having three port portions.

Medical Device Set 200

Figure 15:
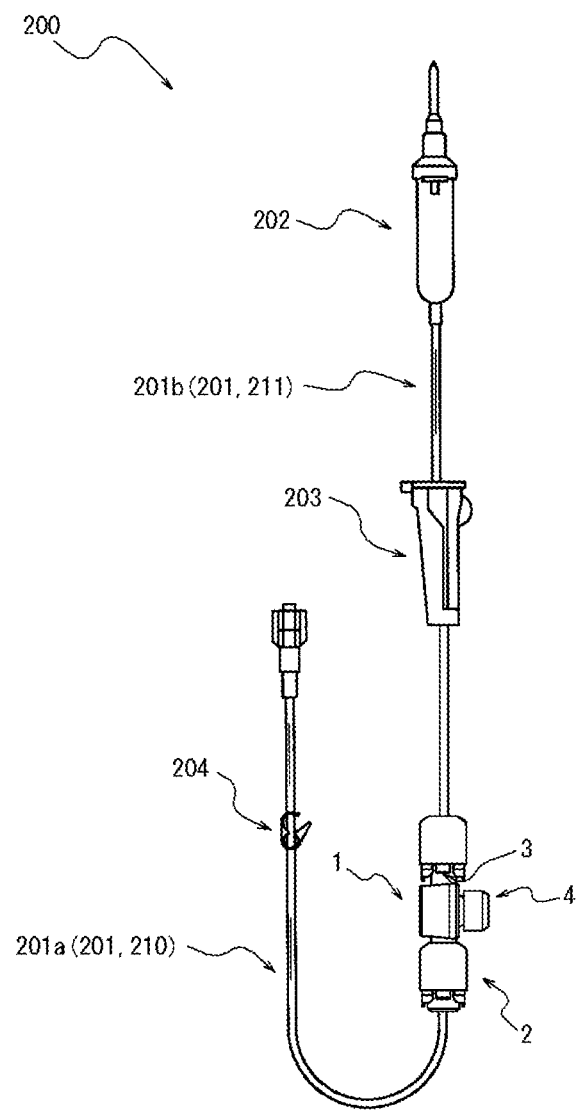
FIG. 15 is a diagram of a medical device set according to one embodiment.

Finally, a medical device set 200 including the connector 1 will be described. FIG. 15 is a diagram of an infusion set as the medical device set 200 including the connector 1. The medical device set 200 illustrated in FIG. 15 includes a T-shaped connector as the connector 1. Alternatively, the medical device set may include a three-way stopcock instead of the T-shaped connector. For the sake of convenience, the medical device set 200 including the T-shaped connector as the connector 1 will be described here.

The infusion set as the medical device set 200 constitutes an infusion line connecting an infusion holding instrument such as an infusion bag not illustrated in FIG. 15 to an indwelling needle not illustrated in FIG. 15. Specifically, the medical device set 200 includes a plurality of medical tubes 201, a drip tube 202 through which the flow rate of an infusion fluid supplied from the infusion holding instrument, an adjustment clamp 203 that is capable of changing the flow rate of the infusion fluid in the medical tubes 201 to a plurality of states, a block clamp 204 that blocks the medical tubes 201, and the connector 1 connecting the plurality of medical tubes 201.

In other words, the medical device set 200 of the embodiment includes the connector 1, a first medical device 210 that has at the upstream end portion a female connector portion equal in shape to the first female connector portion 3 of the connector 1, as a female connector portion connected to the male connector portion 2 of the connector 1, and a second medical device 211 that has at the downstream end portion, a male connector portion equal in shape to the male connector portion 2 of the connector 1, as a male connector portion connected to the first female connector portion 3 of the connector 1.

The plurality of medical tubes 201 in the embodiment includes a first medical tube 201a and a second medical tube 201b. The first medical device 210 in the embodiment is formed from the first medical tube 201a that has an ISO594-prescribed lock-type male connector portion at the downstream end portion and a female connector portion equal in shape to the first female connector portion 3 of the connector 1 at the upstream end portion.

In addition, the second medical device 211 in the embodiment is formed from the second medical tube 201b that has a male connector portion equal in shape to the male connector portion 2 of the connector 1 at the downstream end portion and a bottle needle to be connected to the infusion holding instrument at the upstream end portion.

Figure 16:
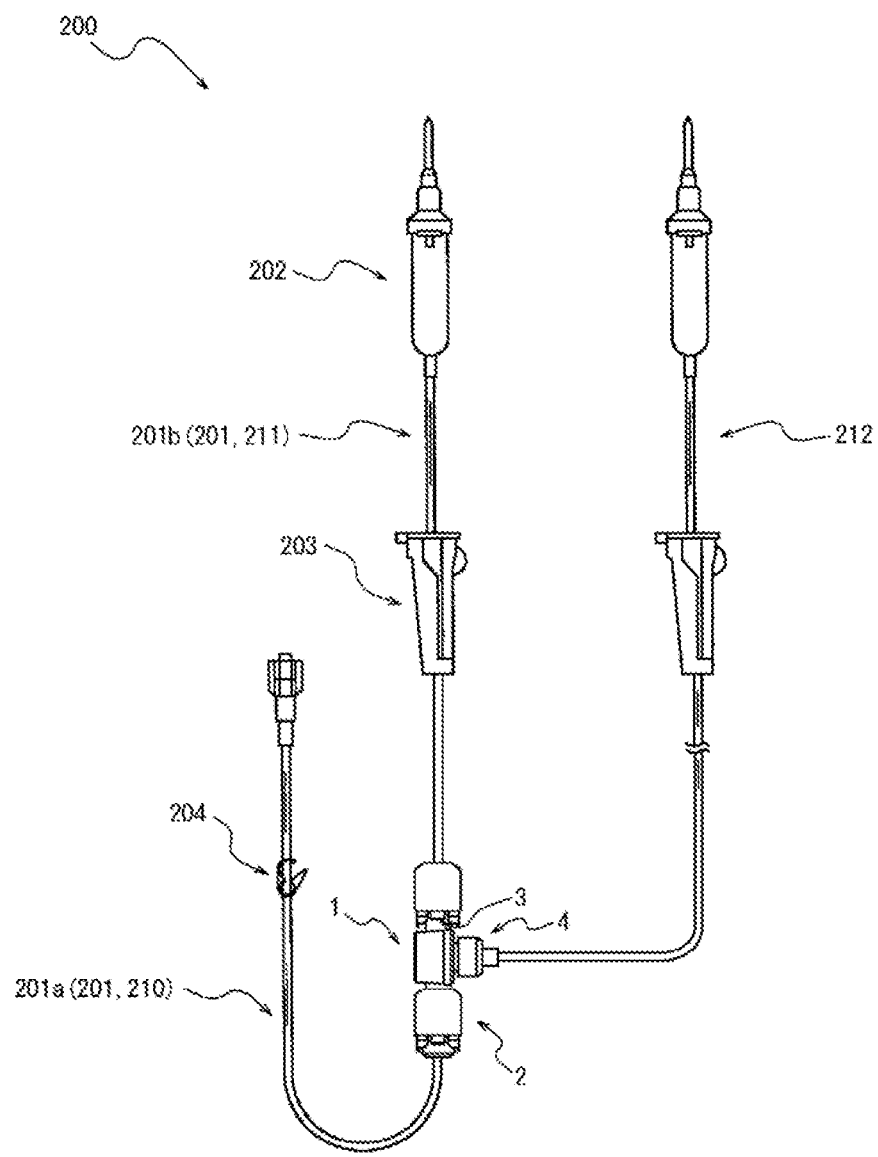
FIG. 16 is a diagram illustrating the state in which a sub line is connected to a main line formed by the medical device set illustrated in FIG. 15.

Then, the upstream end portion of the infusion line in the medical device set 200 illustrated in FIG. 15 is connected to the infusion holding instrument to inject the infusion fluid to a patient. In addition, when there is the need to administer another infusion fluid according to the patient's condition or the like, a branch line can be connected to the second female connector portion 4 of the connector 1. FIG. 16 illustrates the state in which one branch line (sub line 212) is connected to the infusion line (main line) formed from the medical device set 200 illustrated in FIG. 15 via the second female connector portion 4 of the connector 1.

Figure 17:
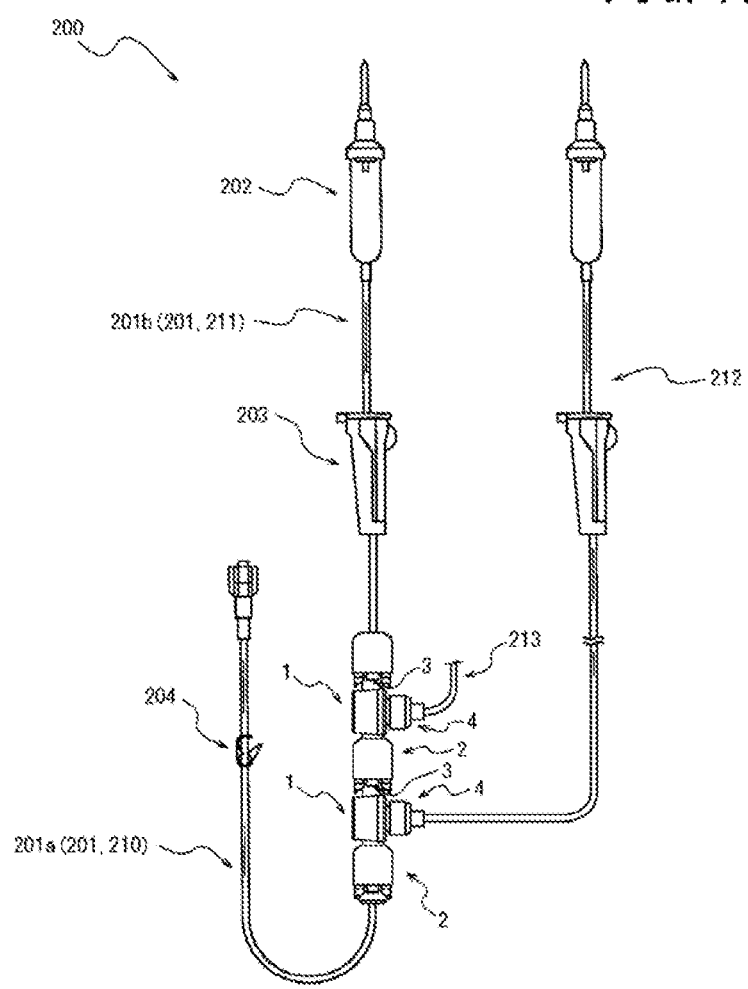
FIG. 17 is a diagram illustrating the state in which another sub line is further connected to the main line in the state illustrated in FIG. 16.

To add a still other sub line according to the patient's condition or the like, as illustrated in FIG. 17, the male connector portion equal in shape to the male connector portion 2 at the downstream end portion of the second medical device 211 in the main line is disconnected from the first female connector portion 3 of the connector 1, another connector 1 is added between the two connector portions, and a branch line (sub line 213) is connected to the second female connector portion 4 of the added connector 1.

In this way, a new sub line can be connected directly to the main line. This facilitates the control of the time from the supply of an infusion fluid via the sub line to the arrival of the infusion fluid at the main line, thereby making it easy to control the amount of dosage per unit time. A still other sub line can be added by the same procedure.

In the medical device set 200 of the embodiment, the main line is disconnected to add a connector 1, and thus medical personnel may touch an infusion fluid such as a drug solution. Accordingly, the female connector portion of the connector is preferably a closed type that blocks the flow path in the connector without connection to the male connector portion. Therefore, the first female connector portion 3 and the second female connector portion 4 of the connector 1 include the first elastic valve body 7 and the second elastic valve body 8. The first elastic valve body 7 and the second elastic valve body 8 are configured to block the second hollow portion 13a and the third hollow portion 14a, that is, block the flow path 5 without connection of the male connector portion. This reduces the risk that medical personnel touches the infusion fluid such as a drug solution at the time of addition of a sub line.

In addition, preferably, the male connector portion 2 of the connector 1 in the medical device set 200 of the embodiment includes the inhibition mechanism (see FIG. 14), and the male connector portion of the second medical device 211 in the medical device set 200 can be connected to and disconnected from the first female connector portion 3 of the connector 1.

According to this configuration, when an another connector 1 is added to the infusion line, the connector 1 and the first medical device 210 in the infusion line cannot be disconnected due to the inhibition mechanism. This forces medical personnel to disconnect the connector 1 and the second medical device 211 and add another connector 1 between them. Specifically, when another sub line is added to the main line to which an existing sub line is connected, it is possible to force medical personnel to add the other sub line to the main line via another connector 1 at the position more upstream than the connection position of the existing sub line (where the connector 1 is located in the main line). Therefore, even when a drug solution including an anticancer agent is administered through the already connected sub line, it is possible to decrease significantly the risk that medical personnel touches the drug solution while adding another sub line.

In the medical device set 200 of the embodiment, the medical tubes 201a and 201b are used as the first medical device 210 including the female connector portion to be connected to the male connector portion 2 of the connector 1 and the second medical device 211 including the male connector portion to be connected to the first female connector portion 3 of the connector 1. However, the medical devices are not limited to medical tubes but may be any medical devices other than medical tubes such as a connector equal in shape to the connector 1 and a connector different in shape from the connector 1. In addition, the first medical device may be formed from a plurality of devices in combination or may be formed from a single device.

REFERENCE NUMERAL LIST 1, 1p, 1q, 101 Connector
2, 2p, 2q, 102 Male connector portion
3, 3p, 3q, 103 First female connector portion
4, 4p, 4q, 104 Second female connector portion
5 Flow path
6 Housing
7, 107 First elastic valve body
8 Second elastic valve body
9, 9q, 109 Claw member
10, 10q, 110 Cover member
11 Housing trunk portion
11a Trunk hollow portion
12 First cylinder portion
12a First hollow portion
13 Second cylinder portion
13a Second hollow portion
14 Third cylinder portion
14a Third hollow portion
15, 115 Slit
16 Slit
17 Holder
18, 118 First cap
19 Second cap
20 Holder main body
21, 121 First holder cylinder portion
22, 122 Second holder cylinder portion
23 Upper cap
24 Lower cap
25, 25a, 25b, 125 Claw portion
26, 126 Distal end portion of first holder cylinder portion
27 Long groove
28 Division portion
29 Protrusion portion (connection inhibition portion)
30, 130 Bottom plate portion of claw member
31a, 31b Side plate portion
32 Concave portion
33 Protrusion portion of claw member
34 Rib
35 Level-difference surface of claw member
36 Bottom plate portion of cover member 37 Cover cylinder portion
38 Level-difference surface of cover member
39 Concave portion
40 Curved portion
41 Flat plate portion
42 Upper annular groove in first elastic valve body
43 Lower annular groove in first elastic valve body
44, 144 Level-difference portion
45a First level-difference surface
45b Second level-difference surface
45c Third level-difference surface
46 Projection portion of second holder cylinder portion
47 Lock projection of second holder cylinder portion
48 Top plate portion of first cap
49 Side wall portion of first cap
50 Lock projection of first cap
51, 510 Guide inclined surface
52 Upper annular groove in second elastic valve body
53 Lower annular groove in second elastic valve body
54 Peripheral surface of second elastic valve body
55 Top plate portion of upper cap
55a Inner peripheral surface of top plate portion
56 Cylinder portion of upper cap
57 Flange portion of upper cap
58 Lock projection of upper cap
59 Screw thread
60 Cylinder portion of lower cap
61 Flange portion of lower cap
62 Lock projection of lower cap
80, 180 First insertion opening
81 Second insertion opening
90 Male connector
150 Flange portion of second holder cylinder portion
151 Cylinder body (first cap)
152 Screw thread
153 Distal end portion
154 Middle portion
155 Proximal end portion
156 First diameter-increased portion
157 Second diameter-increased portion
158 Cylinder body hollow portion (first insertion opening)
159 Head portion of first elastic valve body
160 Cylinder portion of first elastic valve body
161 Flange portion of first elastic valve body
162 Projection portion of cover member
163 Outer edge portion of claw member
164, 165 Surface of projection portion
A Central axis line direction of first holder cylinder portion
B Radial direction of first holder cylinder portion
C Circumferential direction of first holder cylinder portion
D Central axis line direction of second holder cylinder portion (central axis line direction of inner wall defining first insertion opening)
E Circumferential direction of second holder cylinder portion
F Radial direction of second holder cylinder portion
G Central axis line direction of cylinder portion of upper cap (central axis line direction of inner wall defining second insertion opening)
O1 Central axis line of first holder cylinder portion
O2 Central axis line of inner wall defining first insertion opening
O3 Central axis line of inner wall defining second insertion opening
T1 Thickness of bottom plate portion
W1 Width of long groove
W2 Width of concave portion oriented in circumferential direction
W3 Width of division portion oriented in circumferential direction

What is claimed is:

1. A connector comprising:
a male connector portion;
a first female connector portion; and
a second female connector portion;
wherein the connector defines a flow path therein; and
wherein the male connector portion is shaped to be connectable to a first medical device female connector portion that is equal in shape to the first female connector portion;
wherein the male connector portion is shaped to not be connectable to a second medical device female connector portion that is equal in shape to the second female connector portion; and
wherein the male connector portion comprises:
a claw member having a proximal end and a distal end, the claw member comprising a claw portion that is located at the distal end and configured to engage with the first medical device female connector portion that is equal in shape to the first female connector portion, and
a cover member that is moveable along a central axis direction of the male connector between:
a first position at which the cover member extends around both the proximal end of the claw member and at least a portion of the claw portion, and
a second position at which the cover member extends around the proximal end of the claw member but does not extend around the claw portion.

2. The connector according to claim 1, wherein the male connector portion comprises a connection inhibition portion that inhibits connection of the male connector with the second medical device female connector portion that is equal in shape to the second female connector portion.

3. The connector according to claim 1, wherein the male connector portion is located at a first end side of the connector and the first female connector portion is provided at a second end side of the connector that is opposite the first end side.

4. The connector according to claim 3, further comprising:
a housing defining the flow path;
wherein the housing comprises a cylinder portion in the male connector portion at the first end side; and
wherein the housing defines:
a first insertion opening in the first female connector portion communicating with the flow path at the second end side, and
a second insertion opening in the second female connector portion communicating with the flow path at a position different from positions of the cylinder portion and the first insertion opening.

5. The connector according to claim 4, further comprising:
a first elastic valve body that blocks the first insertion opening; and
a second elastic valve body that blocks the second insertion opening.

6. The connector according to claim 1, wherein the first female connector portion is shaped to be connectable to a first medical device male connector portion that is connectable to the second female connector portion.

7. The connector according to claim 6, wherein the first female connector portion comprises:
  a first engagement portion configured to engage with a medical device male connector portion that is equal in shape to the male connector portion, and
  a second engagement portion configured to engage with the medical device male connector portion that is connectable to the second female connector portion at the time of connection.

8. The connector according to claim 7, wherein:
  the first engagement portion is a level-difference portion, and
  the second engagement portion is a male screw portion.

9. The connector according to claim 1, wherein the male connector portion comprises an inhibition mechanism configured to, after connection to the first medical device female connector portion equal in shape to the first female connector portion, inhibit disconnection.

10. A medical device set comprising:
  the connector according to claim 1; and
  a first medical device comprising a medical device female connector portion at a first end portion of the first medical device, the medical device female connector portion being connected to the male connector portion of the connector.

11. The medical device set according to claim 10, further comprising a second medical device comprising a male connector portion at a first end portion of the second medical device, the male connector portion being connected to the first female connector portion of the connector.

12. A medical device set comprising:
  the connector according to claim 9;
  a first medical device comprising a medical device female connector portion at a first end portion of the first medical device, the medical device female connector portion being connectable to the male connector portion of the connector; and
  a second medical device comprising a first medical device male connector portion at a first end of the second medical device, the first medical device male connector portion being connectable to and disconnectable from the first female connector portion of the connector.

13. The connector according to claim 1, wherein the first female connector portion comprises an engagement portion configured to engage with a second medical device male connector portion that is equal in shape to the male connector portion.

14. The connector according to claim 13, wherein the engagement portion is a level-difference portion.

15. The connector according to claim 14, wherein the claw portion is configured to engage with a medical device level-difference portion of the first medical device female connector portion, which is equal in shape to the level-difference portion of the first female connector portion.

* * * * *